(12) United States Patent
Yoganathan et al.

(10) Patent No.: US 10,010,419 B2
(45) Date of Patent: Jul. 3, 2018

(54) PAPILLARY MUSCLE POSITION CONTROL DEVICES, SYSTEMS, AND METHODS

(71) Applicant: GEORGIA TECH RESEARCH CORPORATION, Atlanta, GA (US)

(72) Inventors: Ajit P. Yoganathan, Atlanta, GA (US); Jorge Hernan Jimenez, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 318 days.

(21) Appl. No.: 14/846,932

(22) Filed: Sep. 7, 2015

(65) Prior Publication Data

US 2015/0374494 A1  Dec. 31, 2015

Related U.S. Application Data

(63) Continuation of application No. 12/096,948, filed as application No. PCT/US2006/062185 on Dec. 15, 2006, now Pat. No. 9,125,742.

(60) Provisional application No. 60/750,561, filed on Dec. 15, 2005.

(51) Int. Cl.
*A61F 2/24* (2006.01)

(52) U.S. Cl.
CPC .......... *A61F 2/2445* (2013.01); *A61F 2/2457* (2013.01); *A61F 2250/0004* (2013.01)

(58) Field of Classification Search
CPC ............ A61F 2250/0004; A61F 2/2445; A61F 2/2457
See application file for complete search history.

(56) References Cited

U.S. PATENT DOCUMENTS

| | | | |
|---|---|---|---|
| 3,656,185 | A | 4/1972 | Carpentier |
| 3,671,979 | A | 6/1972 | Moulopoulos |
| 4,055,861 | A | 11/1977 | Carpentier et al. |

(Continued)

FOREIGN PATENT DOCUMENTS

| | | |
|---|---|---|
| EP | 0338994 | 10/1989 |
| EP | 0595791 | 5/1994 |

(Continued)

OTHER PUBLICATIONS

Examination Report for related European Patent Application No. 06850306.9 dated Apr. 8, 2011.

(Continued)

*Primary Examiner* — Gregory Anderson
*Assistant Examiner* — Christina Lauer
(74) *Attorney, Agent, or Firm* — Troutman Sanders LLP; Ryan A. Schneider

(57) ABSTRACT

Papillary muscle position control devices, systems, and methods are provided. According to an exemplary embodiment, a papillary muscle position control device generally comprises a first anchor, a second anchor, and a support structure. The first anchor can be configured to fixedly connect to an in situ valve of a heart ventricle. The second anchor can be configured to fixedly connect to a muscle wall of the valve. The support structure can be configured to have an adjustable length and be coupled to the first anchor and second anchor such that adjusting the length of the support structure varies a distance between the first anchor and the second anchor. Other embodiments are also claimed and described.

18 Claims, 9 Drawing Sheets

(56) References Cited

U.S. PATENT DOCUMENTS

| | | |
|---|---|---|
| 4,056,854 A | 11/1977 | Boretos et al. |
| 4,164,046 A | 8/1979 | Cooley |
| 4,217,665 A | 8/1980 | Bex et al. |
| 4,275,469 A | 6/1981 | Gabbay |
| 4,602,911 A | 7/1986 | Ahmadi et al. |
| 4,790,844 A | 12/1988 | Ovil |
| 4,917,097 A | 4/1990 | Proudian et al. |
| 4,917,698 A * | 4/1990 | Carpentier ............ A61F 2/2448 623/2.36 |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,165,120 A | 12/2000 | Schweich |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Molter et al. |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,669,687 B1 | 12/2003 | Saadat |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,764,510 B2 | 7/2004 | Vidlund et al. |
| 6,790,230 B2 | 9/2004 | Beyersdorf et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,896,690 B1 | 5/2005 | Lambrecht et al. |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,986,775 B2 | 1/2006 | Morales et al. |
| 6,991,649 B2 | 1/2006 | Sievers |
| 7,018,406 B2 | 3/2006 | Seguin et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,186,262 B2 | 3/2007 | Saadat |
| 7,217,284 B2 | 5/2007 | Houser et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,527,647 B2 | 5/2009 | Spence |
| 2001/0034551 A1 | 10/2001 | Cox |
| 2002/0029080 A1 | 3/2002 | Mortier et al. |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2003/0130731 A1 * | 7/2003 | Vidlund ............ A61B 17/00234 623/2.37 |
| 2003/0233142 A1 * | 12/2003 | Morales ............ A61B 17/00234 623/2.37 |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0133192 A1 | 7/2004 | Houser et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075719 A1 | 4/2005 | Bergheim |
| 2005/0075727 A1 | 4/2005 | Wheatley |
| 2005/0080402 A1 | 4/2005 | Santamore et al. |
| 2005/0131533 A1 | 6/2005 | Alfieri et al. |
| 2005/0137689 A1 | 6/2005 | Salahieh et al. |
| 2005/0143811 A1 | 6/2005 | Realyvasquez |
| 2005/0182487 A1 | 8/2005 | McCarthy et al. |
| 2005/0192666 A1 | 9/2005 | McCarthy |

(56) References Cited

U.S. PATENT DOCUMENTS

| | | |
|---|---|---|
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0261759 A1 | 11/2005 | Lambrecht et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020333 A1 | 1/2006 | Lashinski et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0052868 A1 | 3/2006 | Mortier et al. |
| 2006/0149368 A1 | 7/2006 | Spence |
| 2006/0167474 A1 | 7/2006 | Bloom et al. |
| 2006/0195012 A1 | 8/2006 | Mortier et al. |
| 2006/0195183 A1 | 8/2006 | Navia et al. |
| 2006/0229708 A1 | 10/2006 | Powell et al. |
| 2006/0241340 A1 | 10/2006 | Schroeder et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0118154 A1 | 5/2007 | Crabtree |
| 2007/0123979 A1 | 5/2007 | Perier et al. |
| 2007/0129758 A1 | 6/2007 | Saadat |
| 2007/0162111 A1 | 7/2007 | Fukamachi et al. |
| 2007/0173930 A1 | 7/2007 | Sogard et al. |
| 2007/0208357 A1 | 9/2007 | Houser et al. |
| 2007/0213582 A1 | 9/2007 | Zollinger et al. |
| 2007/0255396 A1 | 11/2007 | Douk et al. |
| 2008/0027268 A1 | 1/2008 | Buckner et al. |
| 2008/0039935 A1 | 2/2008 | Buch et al. |
| 2008/0051807 A1 | 2/2008 | St. Goar et al. |
| 2008/0081942 A1 | 4/2008 | Pai et al. |
| 2009/0157174 A1 | 6/2009 | Yoganathan et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| EP | 0860151 | 8/1998 |
| EP | 1034753 | 9/2000 |
| FR | 2708458 | 8/1993 |
| WO | 199119456 | 12/1991 |
| WO | 199503757 | 2/1995 |
| WO | 199640006 | 12/1996 |
| WO | 199741801 | 11/1997 |
| WO | 199742871 | 11/1997 |
| WO | 199806329 | 2/1998 |
| WO | 199911201 | 3/1999 |
| WO | WO199930647 A | 6/1999 |
| WO | 199951169 | 10/1999 |
| WO | 199965423 | 12/1999 |
| WO | 200032105 | 6/2000 |
| WO | WO 2000/047139 | 8/2000 |
| WO | 200119292 | 3/2001 |
| WO | 200126586 | 4/2001 |
| WO | 200147438 | 7/2001 |
| WO | 200187191 | 11/2001 |
| WO | 200203892 | 1/2002 |
| WO | 2003020178 | 3/2003 |
| WO | 2003041617 | 5/2003 |
| WO | 2004004607 | 1/2004 |
| WO | WO 2004/112658 | 12/2004 |
| WO | 2005004753 | 1/2005 |
| WO | 2005034813 | 4/2005 |
| WO | 2005082278 | 9/2005 |
| WO | 2005110290 | 11/2005 |
| WO | 2006041877 | 4/2006 |
| WO | 2006133186 | 12/2006 |
| WO | 2007050506 | 5/2007 |
| WO | 2007100408 | 9/2007 |
| WO | WO2007/100408 | 9/2007 |
| WO | WO2007/100409 | 9/2007 |
| WO | WO2007/100410 | 9/2007 |
| WO | 2007131513 | 11/2007 |
| WO | 2008058940 | 5/2008 |
| WO | 2008063537 | 5/2008 |
| WO | 2008094469 | 8/2008 |
| WO | 2008098226 | 8/2008 |

OTHER PUBLICATIONS

Adams, David, et al., "Large Annuloplasty Rings Facilitate Mitral Valve Repair in Barlow's Disease", The Society of Thoracic Surgeons, vol. 82, pp. 2096-2101, 2006.

Alonso-Lei, F. et al., "Adjustable Annuloplasty for Tricuspid Insufficiency" The Annals of Thoracic Surgery, vol. 46, No. 3, pp. 368-369, Sep. 1988.

Bolling, Steven F. et al., "Mitral Valve Reconstruction in the Patient with Heart Failure", Heart Failure Reviews, vol. 6, pp. 177-185, 2001.

Bolling, Steven F. et al., "Surgical Alternatives for Heart Failure", The Journal of Heart and Lung Transplantation, vol. 20, No. 7, pp. 729-733, 2001.

Carpentier, Alain F. et al., "The "Physio-Ring": An Advanced Concept in Mitral Valve Annuloplasty", The Thirty-First Annual Meeting of The Society of Thoracic Surgeons, pp. 1177-1186, Jan. 30-Feb. 2, 1995.

"Carpentier-Edwards Classic Annuloplasty Ring With Duraflo Treatment Models 4425 and 4525 for Mitral and Tricuspid Valvuloplasty", Baxter Healthcare Corporation, pp. 1-6, 1998.

"Carpentier-Edwards Physio Annuloplasty Ring", Edwards Lifesciences LLC, pp. 1-2, 2003.

Cochran, Richard P. et al., "Effect of Papillary Muscle Position on Mitral Valve Function: Relationship to Homografts", The Society of Thoracic Surgeons, vol. 66, pp. S155-S161, 1998.

Flachskampf, Frank A. et al., "Analysis of Shape and Motion of the Mitral Annulus in Subjects With and Without Cardiomyopathy by Echocardiographic 3-Dimensional Reconstruction", The Journal of the American Society of Echocardiography, vol. 13, pp. 277-287, 2000.

Gatti, Giuseppe et al., "Preliminary Experience in Mitral Valve Repair Using the Cosgrove-Edwards Annuloplasty Ring", Interactive Cardiovascular and Thoracic Surgery, vol. 2, No. 3, pp. 256-261, 2003, http://icvts.ctsnetjournals.org/cgi/content/full/2/3/256.

Melo, J.Q. et al., "Atrioventricular Valve Repair Using Externally Adjustable Flexible Rings", The Journal of Thoracic and Cardiovascular Surgery, vol. 110, No. 5, pp. 1333-1337, Nov. 1995.

"MGH Study Shows Mitral Valve Prolapse Not a Stroke Risk Factor", Massachusetts General Hospital, pp. 1-3, Jun. 1999, http://www.mgh.harvard.edu/DEPTS/pubaffairs/releases/Jun_99_nnitral_valve.htm.

Miller, Craig D., "Ischemic Mitral Regurgitation Redux—To Repair or to Replace?", The Journal of Thoracic and Cardiovascular Surgery, vol. 22, No. 6, pp. 1059-1062, Dec. 2001.

Salgo, Ivan S. et al., "Effect of Annular Shape on Leaflet Curvature in Reducing Mitral Leaflet Stress", Journal of the American Heart Association, Circulation 2002, vol. 106, pp. 711-717, Jul. 22, 2002, http://circ.ahajournals.org/cgi/reprint/106/6/711.

(56) References Cited

OTHER PUBLICATIONS

Seguin, J.R. et al., "Advance in Mitral Valve Repair Using a Device Flexible in Three Dimensions", The St. Jude Medical-Seguin Annuloplasty Ring, The American Society for Artificial Internal Organs Journal, vol. 42, No. 6, pp. M368-M371, 1996.

Smolens, Iva A. et al., "Mitral Valve Repair in Heart Failure", The European Journal of Heart Failure, vol. 2, pp. 365-371, 2000.

"Techniques for 3D Quantitative Echocardiography", University of Washington Cardiovascular Research & Training Center Cardiac Imaging Research Lab, pp. 1-4, http://depts.washington.edu/cvrtc/apples.html.

Watanabe, Nozomi, et al., "Mitral Annulus Flattens in Ischemic Mitral Regurgitation: Geometric Differences Between Inferior and Anterior Myocardial Infarction: A Real-Time 3-Dimensional Echocardiographic Study" Journal of the American Heart Association, Circulation 2005, vol. 112, pp. 458-468, Aug. 30, 2005, http://circ.ahajournals.org/cgi/content/full/112/9_suppl/I-458.

International Search Report and Written Opinion dated Oct. 12, 2007 for related PCT Application No. PCT/US2006/062185.

International Search Report and Written Opinion dated Sep. 27, 2007 for related PCT Application No. PCT/US2006/062192.

International Search Report and Written Opinion dated Oct. 31, 2007 for related PCT Application No. PCT/US2006/062199.

\* cited by examiner

PAPILLARY MUSCLE POSITION CONTROL DEVICES, SYSTEMS, AND METHODS

CROSS REFERENCE TO RELATED APPLICATION

This application is a continuation of U.S. patent application Ser. No. 12/096,948, filed 24 Oct. 2008, which is a 35 U.S.C. § 371 U.S. National Stage of International Application No. PCT/US2006/062185 filed 15 Dec. 2006, which claims priority to and the benefit of U.S. Provisional Application No. 60/750,561, filed 15 Dec. 2005, all of which are hereby incorporated by reference in their entirety as if fully set forth below.

STATEMENT REGARDING FEDERALLY SPONSORED RESEARCH OR DEVELOPMENT

This invention was made with Government support under Contract No. HL052009, awarded by awarded the National Institutes of Health. The Government has certain rights in the invention.

TECHNICAL FIELD

The various embodiments of the present invention relate generally to heart valve repair devices and methods, and more particularly, to devices and methods capable of positioning and controlling papillary muscles of an atrioventricular valve.

BACKGROUND

Cardiovascular disease accounts for nearly fifty percent of deaths in both the developed world and in developing countries. The risk of dying from heart disease is greater than the risk from AIDS and all forms of cancer combined. Cardiovascular diseases cause approximately 12 million deaths in the world each year. It is the leading cause of death in the US, killing approximately 950,000 people each year. It also accounts for a significant amount of disability and diminished quality of life. Indeed, approximately 60 million people in the US alone have some form of heart disease. A great need, therefore, exists for the advancement of devices, methods, systems, and procedures to cure, treat, and correct a wide variety of forms of heart disease.

Normal heart function primarily relies upon the proper function of each of the four valves of the heart, which allow blood to pass through the four chambers of the heart. These four valves have cusps or leaflets, comprised of fibrous tissue, which attach to the walls of the heart. The four chambers of the heart include the right atrium and left atrium, the upper chambers, and the right ventricle and left ventricle, the lower chambers. The four valves, controlling blood flow in and between the chambers, include the tricuspid, mitral, pulmonary, and aortic valves. Heart valves are complex structures that consist of moveable leaflets that open and close the valve. For example, the mitral valve has two leaflets and the tricuspid valve has three leaflets. The aortic and pulmonary valves have three leaflets that are more aptly termed "cusps," as they have a half moon shape.

The cardiac cycle involves the pumping and distribution of both oxygenated and deoxygenated blood within the four chambers. Oxygenated blood, enriched by the lungs, reenters the heart into the left atrium or left upper chamber. The mitral valve, a one way inflow valve, then directs the oxygenated blood into the left ventricle. The contraction of the left ventricle pumps the oxygenated blood through the aortic valve, into the aorta, and into the blood stream. When the left ventricle contracts the mitral valve closes such that the oxygenated blood passes into the aorta. Deoxygenated blood returns from the body via the right atrium. This deoxygenated blood flows through the tricuspid valve into the right ventricle. When the right ventricle contracts, the tricuspid valve closes and the deoxygenated blood is pumped through the pulmonary valve. Deoxygenated blood is directed to the pulmonary vascular bed for oxygenation, and the cardiac cycle repeats itself.

Mitral valve regurgitation is one the most prevalent heart disease conditions, which has many levels of severity. After 55 years of age, some degree of mitral regurgitation is found in almost 20% of men and women who have an echocardiogram. Mitral valve regurgitation, or mitral regurgitation, is a condition in which the mitral valve doesn't close tightly. It results from the failure of the mitral valve leaflets to completely close when the left ventricle contracts, resulting in the flow of blood back into the left atrium due to an overworked left atrium. This allows blood to flow backward in the heart which in turn can lead to serious heart conditions such as congestive heart failure and serious heart rhythm irregularities (arrhythmias). Mitral valve regurgitation is also a progressive condition that, if not corrected, can be fatal.

Also, approximately 40% of patients having some form of surgery in an attempt to correct mitral valve regurgitation end up with either 1+ or 2+ regurgitation measurements. While this may result in improved regurgitation characteristics, the future for these patients can involve additional surgery as their improved regurgitation characteristics will typically degrade over time as 1+ or 2+ regurgitation can negatively affect heart valve functionality.

The function of an atrioventricular valve, like the mitral valve, involves the complex interaction of numerous components, including the leaflets, chordae tendineae, and papillary muscles. If one of the components or functions of the complicated interaction fails, then mitral valve regurgitation can result. For example, excess leaflet tissue, inadequate leaflet tissue, or restricted motion of the leaflets can lead to mitral regurgitation.

Techniques currently exist to assist in correcting the shape of a mitral valve to control the geometries of mitral valve shape. For example, one conventional technique includes surgically reshaping the ventrical with extensive surgical manipulation. Another conventional technique involves reshaping the geometry of the annulus of the ventrical with a ring or other annuloplasty device. Another conventional device is the Coapsys Device manufactured by Myocor, Inc. (Maple Grove, Minn. USA) and described in U.S. Pat. Nos. 6,332,893 and 7,077,862.

These conventional techniques, while serving their respective purposes, do posses drawbacks. For example, certain of these conventional techniques, can at times, require extensive surgery which can increase possible associated risks to patients. Also, these techniques do not utilize an atrioventricular valve's papillary muscles to assist in reshaping valve geometry by apically adjusting a papillary muscle to control valve regurgitation. Further, these conventional devices do not enable fine tuning adjustments to be made on a beating heart to control, reduce, and eliminate blood regurgitation in atrioventricular valves.

Accordingly, there is a need for devices and methods to control the position of papillary muscles relative to an annulus of an atrioventricular valve. In addition, there is a need for devices and methods to reposition a papillary muscle using a positioning device to assist in controlling, reducing, and eliminating blood regurgitation. Still yet, there is a need for devices and processes enabling apical adjustability of positions between papillary muscles and an annulus of an associated atrioventricular valve. There is still yet a further need for devices and methods enabling fine tuning adjustments to be made on a beating heart to control, reduce, and eliminate blood regurgitation in atrioventricular valves. It is to the provision of such papillary muscle positioning devices, systems, processes, and methods that the various embodiments of the present invention are directed.

BRIEF SUMMARY

Embodiments of the present invention provide devices and methods capable of controlling positioning of papillary muscles and an annulus of an atrioventricular valve. According to some embodiments, the present invention comprises methods, implants, and tools enabling control of a relative position between papillary muscles of an atrioventricular valve and an associated annulus to aid in reshaping the geometry of the annulus to control, reduce, and eliminate blood flow regurgitation. Some embodiments can be used with an annuloplasty device, and other embodiments may not use an annuloplasty device.

Generally described, a papillary muscle positioning device can comprise a first anchor, a second anchor, and a support structure. The term anchor is at times used synonymously with pad herein. The first anchor can be configured to fixedly connect to an in situ valve of a heart ventricle, and the second anchor can be configured to fixedly connect to a muscle wall of the valve. The support structure can be configured to have an adjustable length and coupled to the first anchor and second anchor. In this configuration, the length of support structure can be adjusted to vary a distance between the first anchor and the second anchor, which in turn can vary the distance between the in situ valve and the muscle wall.

A device embodiment of the present invention can also include additional features. For example, the first anchor can be an annuloplasty ring secured to an annulus of the valve. The second anchor can penetrate the muscle wall at a papillary muscle to enable the adjustable length support structure to vary a distance between the papillary muscle and the first anchor. Still yet, a device can further comprise one of an internal restraint disposed within the valve or an external restraint disposed about an exterior of the valve. These restraint can alter a lateral position of the papillary muscle.

Still yet other features are also contemplated for devices according to the present invention. For example, the support structure can have a generally circular or generally square cross-sectional shape. The first anchor and the second anchor can comprise a lock to engage the support structure. The support structure can comprise an internal locking region to enable the length of the support structure to be locked of fixed. The first anchor can be an annulus anchor comprising flexible arms that extend at least partially around a perimeter of the annulus. The first anchor can comprise a connection mechanism adapted to connect to an annuloplasty device. And the support structure can comprise interior corresponding threaded regions enabling the length of the support structure to be adjusted.

Embodiments of the present invention also include methods to position a papillary muscle. Broadly described, a method to control a distance between a valve muscle and a valve annulus in a human heart can comprise providing a device configured to be positioned between a valve muscle and a valve annulus; disposing the device between the valve muscle and the valve annulus; and adjusting a length of the device to alter the distance between the valve muscle and the valve annulus. A positioning method can also comprise attaching the device to at least one of an annulus ring or a papillary muscle. Another feature of a positioning method can include rotating one end of the device relative to another end of the device to adjust the length of the device.

Other method embodiments of the present invention can include additional steps. For example, a method can comprise flexing one end of the device relative to another end of the device to adjust the length of the device. Also, a method can comprise attaching the device to at least one exterior area proximate a papillary muscle of the valve muscle, or providing a tension member to tension the valve muscle to change the shape of the valve muscle. The valve muscle can be a papillary muscle having a tip, and one end of the device can be attached to the tip of the papillary muscle. Also, one end of the device can be attached proximate the base of the papillary muscle one end of the device can secured to at least a portion of the exterior of the papillary muscle. The device can be provided with corresponding internal locking members adapted to adjust the length of the device according to some methods. And according to some methods, the device can comprise multiple support structures each connected to a separate papillary muscle. The multiple support structures can have adjustable lengths to alter the distance between the valve muscle and the valve annulus.

According to another embodiment of the present invention, a papillary muscle position system can comprise a first support structure and a first adjustment mechanism. The first support structure can be coupled to a first papillary muscle and the first adjustment mechanism can be coupled to the first support structure to adjust the length of the first support structure to position the first papillary muscle. A system can also comprise a second support structure coupled to a second papillary muscle, and a second adjustment mechanism coupled to the second support structure to adjust the length of the second support structure to position the second papillary muscle. A system can also include an annuloplasty device coupled to an annulus of an atrioventricular valve and coupled to the first and second adjustment mechanisms. In this configuration, the first and second adjustment mechanisms can be positioned proximate the annulus. Also, a system can comprise an anchor disposed proximate the first papillary muscle. The anchor can receive the first support structure so that the first support structure is coupled to the first papillary muscle.

Other features are also contemplated according to additional system embodiments. For example, an anchor can be attached to one of the exterior of the first papillary muscle or beneath the first papillary muscle on an exterior surface of an associated valve wall. Also, the support structure can be a suture that is looped about the first papillary muscle. In another configuration, the first adjustment mechanism can comprise threaded components that interact with each other to adjust a length of the first support structure. One of the treaded components can be coupled to the first support structure. Alternatively, the first adjustment mechanism can comprise a pin to lockably engage the first support structure to fix the length of the first support structure. The first support structure can be a semi-rigid elongated rod that flexes in a substantially unidirectional manner. And the first support structure can house an internal security wire to secure the first support structure according to some embodiments.

Still yet, other embodiments of the present invention include additional method embodiments. According to other method embodiments, a method to position a papillary muscle can comprise coupling a first end of a support structure to a papillary muscle; coupling a second end of the support structure proximate an annulus of a valve; and adjusting the position of the papillary muscle in a substantially apical direction with an adjustment device so that the papillary muscle is positioned closer to the annulus. A method can also comprise providing an anchor proximate the papillary muscle, the anchor to receive the first end of the support structure. A method can also include coupling the adjustment device to an annuloplasty device coupled to the annulus. Another method embodiment can comprise positioning the adjustment device proximate at least one of the papillary muscle or the annulus. Compressing a papillary muscle to alter at least one of the shape, position, or length of the papillary muscle can also be included in a method embodiment.

In yet another embodiment of the present invention, a papillary muscle positioning device generally comprises a support structure and an adjustment mechanism. The support structure can be disposed between a papillary muscle and an annulus. The adjustment device can lockably engage the support structure to alter the length of the support structure and to fix the length of the support structure at an altered length. The adjustment device can be attached proximate to at least one of the annulus, an annuloplasty device coupled to the annulus, the papillary muscle, or disposed partially within the papillary muscle. Also, at least one of the support structure or the adjustment device can comprise threaded components. In this configuration, the threaded components can interact with each other in response to an applied mechanical force such that one of the threaded components can move relative to and lockably engage the other threaded component.

Accordingly, it is an aspect of some embodiments of the present invention to provide a cardiovascular implant to control the geometry, size, and area of an annulus of an atrioventricular valve and the relative position between papillary muscles and an annulus of an atrioventricular valve.

Another aspect of some embodiments of the present invention is to control the relative position between papillary muscles and an annulus of an atrioventricular valve.

Another aspect of some embodiments of the present invention is to provide a cardiovascular implant to control the apical position between papillary muscles and an annulus of an atrioventricular valve Other aspects according to some embodiments of the present invention include providing a cardiovascular implant to control the chordal force distribution of an atrioventricular valve or to reduce the length of a papillary muscle.

Still yet other aspects according to some embodiments of the present invention include providing a cardiovascular implant which may be delivered percutaneously or thoroscopically to control a relative position between papillary muscles and an annulus of an atrioventricular valve.

Still yet another aspect according to some embodiments of the present invention includes providing a cardiovascular implant that can be fine tuned and adjusted on a beating heart to control, reduce, and eliminate blood flow regurgitation.

Other aspects and features of embodiments of the present invention will become apparent to those of ordinary skill in the art, upon reviewing the following description of specific, exemplary embodiments of the present invention in conjunction with the accompanying figures.

DETAILED DESCRIPTION OF PREFERRED & ALTERNATIVE EMBODIMENTS

Figure 1:
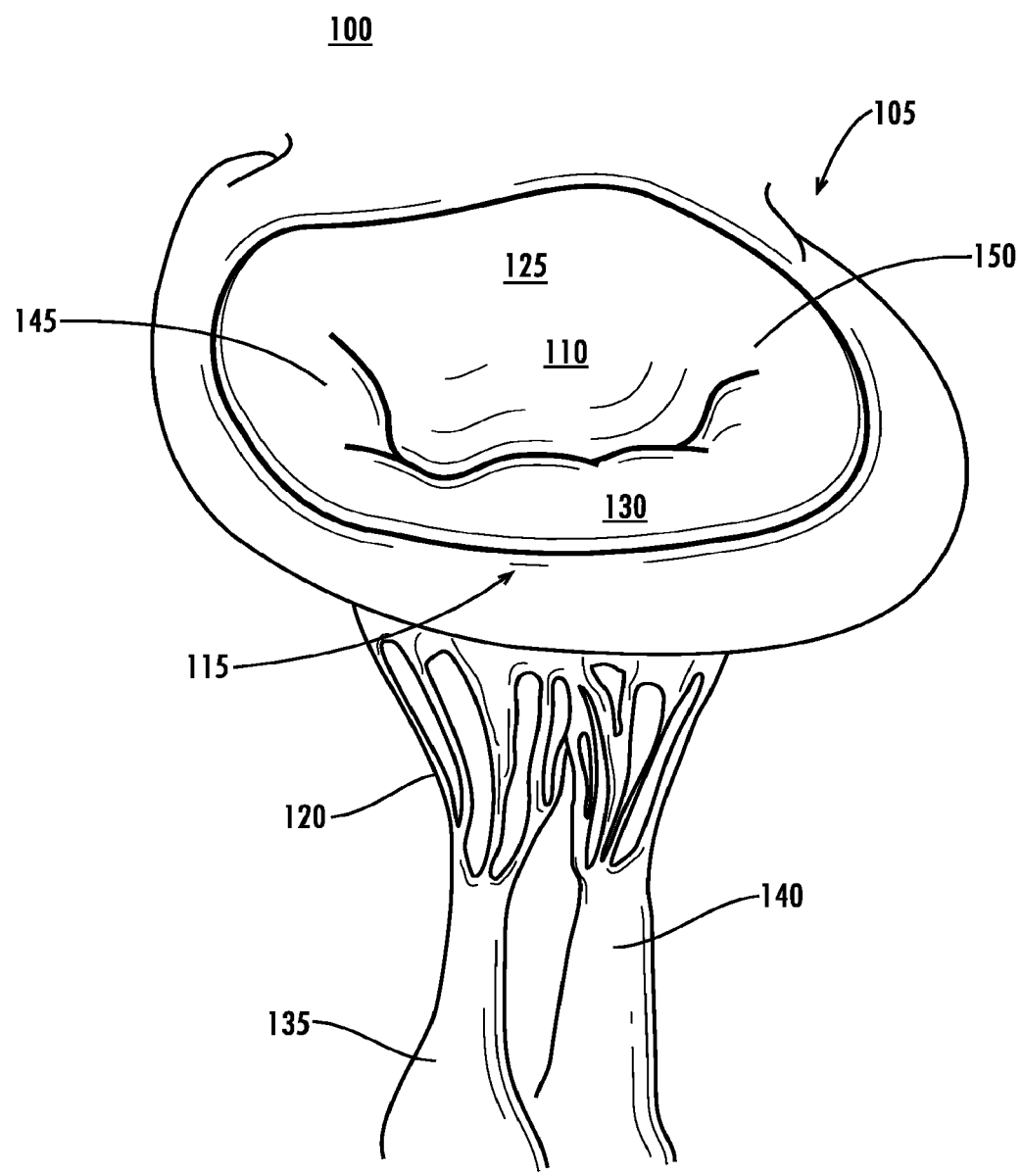
FIG. 1 illustrates a perspective view of a mitral valve and certain other components associated with a mitral valve.

Referring now to the figures, wherein like reference numerals represent like parts throughout the several views, exemplary embodiments of the present invention will be described in detail. Throughout this description, various components may be identified having specific values or parameters, however, these items are provided as exemplary embodiments. For example, it should be understood that while some embodiments are discussed with specific reference to mitral valves, embodiments of the present invention can be utilized in conjunction with any atrioventricular valve. Thus, the exemplary embodiments do not limit the various aspects and concepts of the present invention as many comparable parameters, sizes, ranges, and/or values may be implemented.

FIG. 1 illustrates a mitral valve 100. As shown, the mitral valve 100 includes a mitral annulus 105, an anterior mitral leaflet 110, a posterior mitral leaflet 115, chordae tendineae 120, and medial and lateral papillary muscles 135, 140. Mitral annulus refers to the elliptical region of the valve leaflet attachment contiguous with the base of the left atrium. The mitral annulus 105 is composed of anterior mitral annulus 125 and a posterior mitral annulus 130. The mitral annulus 105 is saddle shaped with the basal portions of the saddle located medially and laterally. Attached to the anterior mitral annulus 125 is the anterior mitral leaflet 110 and attached to the posterior mitral annulus 130 is the posterior mitral leaflet 115. The regions where the anterior mitral leaflet 110 and the posterior mitral leaflet 115 meet are termed the lateral commissure 145 and the medial commissure 150.

The various components of the mitral valve 100 depicted in FIG. 1 control blood flow within a heart between the left atrium and left ventricle of the heart. In a normal mitral valve, when the atrial pressure exceeds the ventricular pressure, the valve leaflets 110, 115 open in to the ventricle. When the ventricle pressure increases, the leaflets meet and close, covering the area of the valve annulus 105. Therefore, as shown in FIG. 1, the anterior mitral leaflet 110 and the posterior mitral leaflet 115 will open during systole to allow blood to flow through the mitral valve 100. Conversely, the anterior mitral leaflet 110 and the posterior mitral leaflet 115 will overlap and close the mitral valve 100 to prevent regurgitation, into the left atrium. As people age and due to other factors, the mitral valve 100 and its components can stop functioning correctly thereby allowing regurgitation of blood.

As part of their discovery of the various embodiments of the invention discussed herein, the inventors performed several studies. These studies led the inventors to conclude that controlling the position of papillary muscles of an atrioventricular valve can enable an abnormal atrioventricular valve to have normal functional characteristics. With respect to a mitral valve, such normal functional characteristics include improved closure between valve leaflets 110, 115 (or leaflet malcoaptation) to help control, reduce, and eliminate regurgitation between the left atrium and left ventricle of the heart. In addition to discussing various embodiments of the present invention below, certain of the inventor's study results and methodologies are also provided to further explain concepts and details associated with various embodiments of the present invention.

Discussion of Study Methodologies and Study Results

Figure 2:
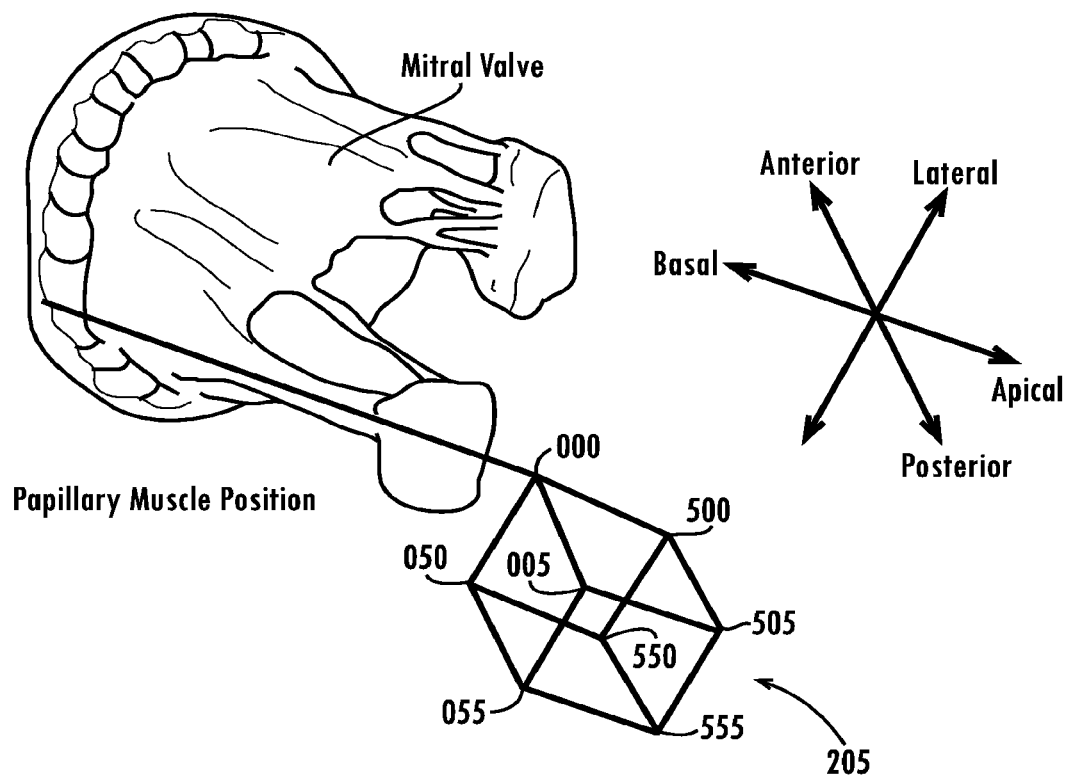
FIG. 2 illustrates a spatial reference system based on normal papillary muscle position that the inventors used during a study of papillary muscle position.

The inventors studied seven human and four porcine valves using a left heart simulator with a standard atrial model. Variations in chordal force and mitral regurgitation due to papillary muscle displacement utilize a normal papillary muscle position as a reference for the study. The papillary muscles were displaced to eight different papillary muscle positions. FIG. 2 illustrates a spatial reference system based on normal papillary muscle position that the inventors used during a study of papillary muscle.

The reference for the displacements illustrated in FIG. 2 is the normal papillary muscle position. All papillary muscle displacements were symmetrical in the study; therefore both papillary muscles were displaced equally to reach each position. All papillary muscle positions were constructed from 5 mm vectorial displacements from the normal position in the apical, lateral, and posterior directions in the study. Illustrated in FIG. 2 is a displacement reference system 205 that shows the various displacement positions used by the inventors in their studies. The below table (Table I) summarizes the vectorial compositions of the papillary muscles that the inventors used with the displacement reference system 205 illustrated in FIG. 2.

TABLE I

| Papillary Muscle | Displacement (millimeters) | | |
| --- | --- | --- | --- |
| Position | Apical | Lateral | Posterior |
| 000 | 0 | 0 | 0 |
| 005 | 0 | 0 | 5 |
| 050 | 0 | 5 | 0 |
| 055 | 0 | 5 | 5 |
| 500 | 5 | 0 | 0 |
| 505 | 5 | 0 | 5 |
| 550 | 5 | 5 | 0 |
| 555 | 5 | 5 | 5 |

During the cardiac cycle, the mitral valve is held within a very dynamic environment which is described by annulus displacement, ventricular motion, and papillary muscle contraction. Within this environment, the basal chords maintain a relatively constant distance from the tips of the papillary muscles to the annulus, aiming to maintain overall valve geometry and isolating the motion of the leaflets from the surrounding environment movement. The geometrical and anatomical construct of the mitral valve must ensure that the chords controlling coaptation and especially those involved in the appropriate sealing of the valve are less sensitive to the changing environment. Therefore, the intermediate chords are less sensitive to changes in papillary muscle position than the basal chords, whereas the marginal chords are the least sensitive of all chordal types to papillary muscle position variations.

These characteristics were clearly shown by the standard deviations of the forces of the chords when different papillary muscle positions were compared. In addition, the direction of displacement of the papillary muscles was directly related to which chord type presented altered tensions. For example, apical displacement affected tension on the secondary chords of both leaflets, whereas posterior displacement tended to reduce the force on chords which inserted into the posterior leaflet. The tensions on chords which inserted near the annulus were affected by displacement of the papillary muscles in all directions. Apical displacement significantly increased the tension present on the anterior strut chord. When the papillary muscles are displaced apically, the coaptation geometry of the mitral valve changes. Thus, apical displacement generates tented leaflet geometries, and under a tented geometry, the intermediate chords restrict leaflet motion.

The study results for the anterior strut chord showed that as apical displacement of the papillary muscles tented the leaflets and significantly increased the load the anterior strut chord. The decrease in force when repositioning the papillary muscles from position 500 to position 505 was probably related to a redistribution of the load between chords. Posterior papillary muscle displacement decreased the tension on the posterior intermediate chord by approximately 37%. This papillary muscle relocation shifted the coaptation line posteriorly, reducing the area of the orifice covered by this leaflet and decreasing the insertion angle of this chord. Both of these changes reduced the resultant force vector. The increase in tension associated with position 500 is explained by the same tenting described for the anterior strut chord.

Combined apical-lateral displacement induced a significant increase in tension due to tenting of the leaflet and the stretching and redirection of the posterior intermediate chord. This effect was reduced in position 555 because of the posterior motion associated with this position. The force on the anterior marginal chord and posterior marginal chord was relatively homogeneous for the different papillary muscle positions. As the marginal chords control coaptation in the tip of the leaflet, tension in them may be less sensitive to changes in papillary muscle position as the mitral valve is designed to operate in a highly dynamic environment. The tension on the posterior basal chord was highly sensitive to papillary muscle displacement. Posterior displacement reduced the tension on the posterior basal chord as it redirected the angle of the chord. This motion reduced the septal lateral component of force, and thus reduced the overall resultant force. As chordae tendineae have a non-linear mechanical response to elongation, apical displacement increased peak systolic tension on the basal posterior chord because of pre-straining. A pre-strained chord will be subjected to a higher tension for a similar strain during coaptation. Lateral displacement of the papillary muscles reduced the force on the basal posterior chord. This reduction was probably due to a redistribution of the load with other chords.

The commissural chord selected experiments inserted near the annulus and below the septa lateral midpoint of the valve (posterior section of the valve); therefore, trends in force variation due to papillary muscle displacement were similar to those present in the basal posterior chord. Similarly, pre-straining increased the force on the basal posterior chord during apical motion of the papillary muscles. In addition, both posterior and lateral relocation of the papillary muscles decreased the force on these chords. The relative contributions of these motions (lateral, posterior) to the force on the commissural chord should be different than the contributions to the force of the basal posterior chord because of their different angle and location of insertion on the valve.

Finally, positions associated with apical displacement (500, 505, 550, 555), showed clinically significant levels of mitral regurgitation (>20%). Other positions associated with lateral or posterior displacement of the papillary muscle did not induce clinically relevant mitral regurgitation. Only position 505 associated with both lateral and posterior displacement showed an increase in regurgitation.

The study results revealed the effects of papillary muscle displacement on the peak systolic tension present on different types of chordae tendineae. Apical motion increased peak systolic tension on the secondary chords, whereas chords on the posterior side of the valve were subject to a reduction in peak systolic tension after posterior motion of the papillary muscles. Chords which insert near the annulus were affected by lateral, posterior, and apical displacement of the papillary muscles. The study results also showed that variation in tension due to papillary muscle relocation decreased with increasing distance of chordal insertion from the mitral annulus. Chords which insert near the annulus are the most sensitive to variations in papillary muscle position, whereas chords which insert into the tip leaflet are the least sensitive to papillary muscle relocation. Additionally, mitral regurgitation was associated with apical displacement of the papillary muscles, and therefore may also be associated with increased tension of the intermediate or basal chords.

A second study on papillary muscle displacement was designed to elucidate the interaction between annular dilation and both symmetrical and asymmetrical papillary muscle displacement. The porcine mitral valves mounted in a normal sized annulus and in a normal papillary muscle position closed efficiently, with a central coaptation length of approximately 15.8±2.1 mm, and without echodetectable mitral regurgitation. With dilated mitral annuli and/or displaced papillary muscles, regurgitation occurred. The measured central coaptation lengths decreased with annular dilation and papillary muscles displacement. Coaptation length reached its minimum value of approximately 0.4±0 5 mm while using the large annulus and under symmetrical papillary muscle displacement.

Mitral regurgitation volume increased with annular dilation and papillary muscle displacement. The volume reached approximately 18.5±10.2 ml with the large annulus under symmetrical papillary muscle displacement. Regurgitation volume correlated with central coaptation length (r=approximately 0.71). Asymmetric tethering of the posterior papillary muscle led to mitral regurgitation volumes of approximately 4.1±1.9; 12.4±4.3; and 20.1±12.5 ml for the normal, medium, and large annuli, respectively. Asymmetric anterior papillary muscle tethering led to regurgitation volumes of approximately 3.6±1.8; 10.5±3.5; and 19.6±9.9 ml for the normal, medium, and large annuli, respectively.

Increased distance between the anterior and posterior annuli in the dilated mitral annular model decreased leaflet coaptation length, shifting the coaptation line towards the edges of the leaflets. This describes how a larger orifice has to be covered by the same amount of tissue; therefore the overlapping of the leaflets is reduced. Clinical observations of extensive left ventricular infarction, or left ventricular dilation, have shown that both papillary muscles move in the radial direction away from the center of the left ventricle. The apical posterior lateral papillary muscle displacement performed in the inventor's study simulated this condition. Indeed, apical displacement was restricted by the chordae tendineae because of their stiffness. This is consistent with measurements by others, who observed that the distance between the tips of the papillary muscle and the mitral annulus is relatively constant. Both the anterior and posterior mitral leaflets were restricted during systole with symmetrical papillary muscle displacement.

Symmetrical papillary muscle displacement induced the coaptation line to shift towards the ventricle parallel to the annulus plane, and produced leakage gaps and regurgitation in the central region of the valve. This is similar to the phenomenon observed in patients with extensive myocardial infarction, where the area of the roots of both papillary muscles may be affected, leading to subsequent relocation. Regional myocardial infarction produces local effects which may result in uneven papillary muscle displacement, especially if the area affected involves only one of the papillary muscles. Asymmetric papillary muscle displacement restricted leaflet motion on the tethered side of the valve. Commissural leaflets appeared to be more affected by papillary muscle displacement, because they are shorter than the posterior and anterior leaflets, and are therefore characterized by a smaller coaptation area. With a dilated annulus and under papillary muscle tethering, the commissural leaflets decreased their coaptation area and developed leakage gaps. Furthermore, tethering only one papillary muscle (i.e., asymmetric tethering) led the commissural leaflet on the opposite side of the valve to bulge towards the atrium during systole, as a result of relative slackness in the chordae tendineae in this area of the valve.

These observations, which describe irregular tenting and bulging of the leaflets, are consistent with observations in experiments using an in-vivo ovine model of acute infarction of the posterior left ventricular wall. Increased tension on one commissural side leads to an uneven coaptation with off-centered gaps and consequently significant mitral regurgitation on the tethered side of the valve, which is also consistent with clinical observations, where the regurgitation Jets were found on the side of the infarction. Ischemic myocardial infarction may also restrict anterior leaflet motion and generated posterior leaflet prolapse.

Leaflet geometry during valve closure was affected by annular dilation and papillary muscle position. Symmetrical papillary muscle displacement caused leakage gaps in the central region of the coaptation line and subsequent regurgitation. Asymmetric papillary muscle tethering caused tethered side leakage gaps and moderate to severe regurgitation. Tenting and bulging of the commissural leaflets generated vulnerable points for mitral regurgitation under these conditions. In general under similar conditions of annular dilation asymmetric papillary muscle displacement induced larger regurgitation volumes than symmetric papillary muscle displacement.

In summary, the inventor's studies showed that papillary muscle displacement are associated with mitral regurgitation. Increased annular area reduces leaflet coaptation resulting in regurgitation. In addition papillary muscle displacement can produce leaflet malcoaptaion and subsequent regurgitation. The inventors also found that the regurgitation due to papillary muscle displacement was more severe when the papillary muscles are displaced asymmetrically. The inventors also discovered that apical displacement is an important determinant of regurgitation due to papillary muscle displacement.

Apical displacement affects the tension on the intermediate chords restriction leaflet motion. Thus, controlling papillary muscle position was found to be a factor to correct mitral regurgitation. Considering that there is a constant distance between the commissural areas of the annulus and papillary muscles, this distance can be controlled by the below discussed various embodiments of the present invention to restore normal valve functions to an abnormal functioning atrioventricular valve.

Discussion of Embodiments

Figure 3:
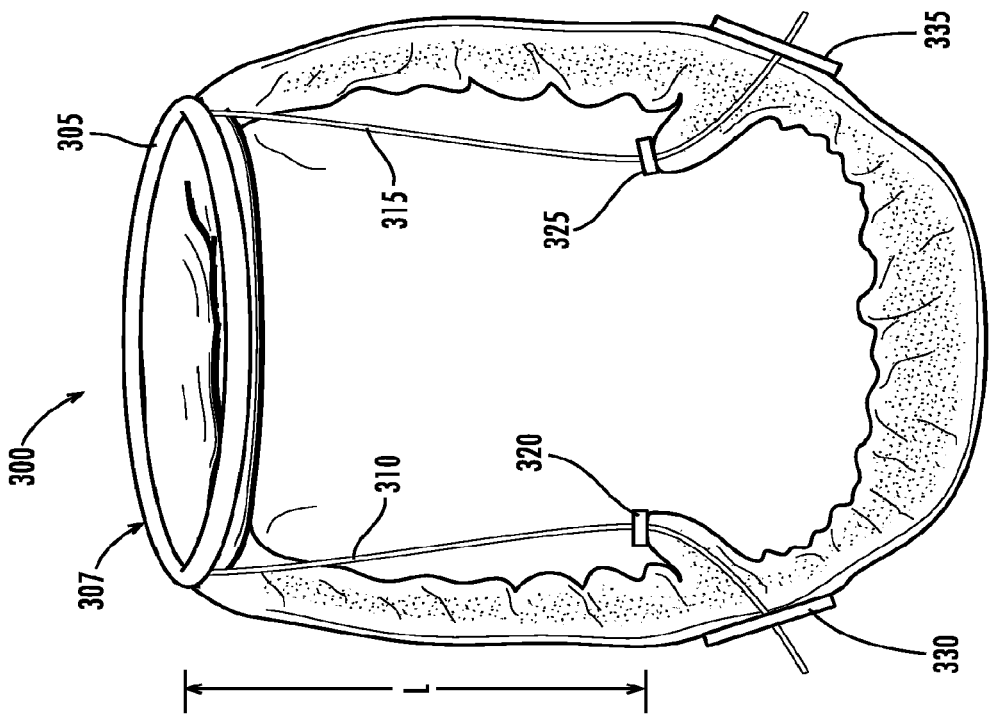
FIG. 3 illustrates a device to control the position of multiple papillary muscle including an annular ring according to some embodiments of the present invention.

Turning now specifically to the other figures, FIG. 3 illustrates a device 300 that includes papillary muscle support structures to control papillary muscle position according to some embodiments of the present invention. The device 300 is configured to enable control of a distance along line L between the annulus and the tip of the papillary muscles. The distance along line L is at times referred to herein as the apical distance between papillary muscles and an associated atrioventricular valve.

As shown in FIG. 3, the device 300 has various components. These components can include an annuloplasty device 305, a first support structure 310, a second support structure 315, a first papillary muscle pad 320, a second papillary muscle pad 325, a first ventrical wall pad 330, and a second ventrical wall pad 335. As shown, the two support structures 310, 315 are disposed and coupled between the annuloplasty device 305 and a respective papillary muscle pad and ventrical pad. More specifically, the first support structure 310 is coupled between the annuloplasty device 305, and the first papillary muscle pad 320 and the first ventrical wall pad 330. Similarly, the second support structure 315 is coupled between the annuloplasty device 305, and the first papillary muscle pad 325 and the first ventrical wall pad 335. As discussed below in greater detail, other embodiments may utilize a single support structure, may not include an annuloplasty device, or may utilize different mechanisms to attach to an annuloplasty device and a papillary muscle.

Preferably the device 300 enables the support structures 310, 315 to move so that the length of line L can vary. For example, the papillary muscle pads 320, 325 and the ventrical wall pads 330, 335 can be adapted to enable movement of the support structures 310, 315 such that the length of the support structures can be adjusted or varied. According to some embodiments, one or both of the papillary muscle pads 320, 325 and ventrical wall pads 330, 335 can include locking mechanisms or other pressure mechanisms to enable the distance between a papillary muscle and an annulus to be adjusted and fixed at a certain length. For example, the pads can comprise a clamping or pin mechanism that will fix the support structures 310, 315 in a static position. The movement of the papillary muscle relative to the annulus can alter or change the geometric shape of valve leaflets to control, reduce, and eliminate regurgitation.

The annuloplasty device 305 can have various characteristics. Indeed, according to some embodiments, the annuloplasty device 305 can have a proximal ring 307. The proximal ring 307 may be rigid, flexible, complete, partial, or comprise multiple links. The proximal ring 307 may also be constructed of a biocompatible material or of a non biocompatible material covered by a biocompatible layer. For example, the proximal ring 307 may be constructed of a biocompatible metal or biocompatible polymer. The proximal ring 307 may be covered by a suturing layer which will allow it to be attached using sutures to the annulus. The proximal ring 307 may be attached on or to the annulus of an atrioventricular valve using clamps, hooks, sutures, or other anchoring mechanisms.

As mentioned above, the support structures 310, 315 can be coupled to the annuloplasty device 305 according to some embodiments. The annuloplasty device 305 may permanently or temporarily be coupled to or engage the support structure 310, 315. For example, the support structures 310, 315 can be manufactured integrally with the annuloplasty device 305 to form a unitary device or the supports structures 310, 315 can be manufactured separately from the annuloplasty device 305. For embodiments where the support structures 310, 315 are not permanently coupled to the annuloplasty device 305, the support structures 310, 315 can include attachment members that enable the support structures 310, 315 to connect to any annuloplasty device. This advantageous feature of certain embodiments of the present invention enables use with an annuloplasty device already deployed or implanted within a patient, or an annuloplasty device manufactured by a different manufacturer. Alternatively, the support structures 310, 315 can comprise clamps to enable the support structures 310, 315 to clamp onto an annuloplasty device 305. Other techniques for coupling support structures to an atrioventricular valve annulus or annuloplasty device are discussed below.

The support structures 310, 315 of the device 300 can also have various characteristics. As mentioned above, and as shown in FIG. 3, the support structures 310, 315 can be connected to a papillary muscle and the annuloplasty device 305. Alternatively, the support structures 310, 315 may be connected between a papillary muscle and an annulus of an atrioventricular valve or a wall of an atrioventricular valve. The support structures 310, 315 may be an elongated rod, wire, suture, or many other similar tension members. The support structures 310, 315 may be constructed of numerous materials, including but not limited to, a biocompatible metal, biocompatible polymer, biocompatible silk, other biocompatible materials, collagen, bio-engineered chords, or other bio-engineered materials. The support structures 310, 315 can also be slidably coupled to or otherwise interact with the pads 320, 325, 330, 335 enabling the apical distance L to be adjusted and fine tuned after implantation of the device 300.

The pads 320, 325, 330, 335 of device 300 can have various characteristics. More specifically, the papillary muscle pads 320, 325 preferably enable the support structures 310, 315 to pass through (or penetrate) a papillary muscle so that the papillary muscle is not damaged and so that the support structures 310, 315 do not entangle among the several chords associated with a papillary muscle. As shown, the papillary muscle pads 320, 325 can be attached or secured to a tip of a papillary muscle. In other embodiments, the papillary muscle pads 320, 325 may have other configurations that allow the papillary muscle pads 320, 325 to be attached or secured along the exterior of or proximate the base of a papillary muscle. An exemplary configuration can include a donut shaped papillary muscle connection device. The ventrical wall pads 330, 335 preferably provide a support on the exterior of a ventrical wall so that a support structure can be securedly affixed to the ventrical wall pads 330, 335. The ventrical wall pads 330, 335 can have various lengths.

The pads 320, 325, 330, 335 of device 300 can connect to the support structures 310, 315 in numerous configurations. According to some embodiments, the attachment pads 320, 325, 330, 335 can include an aperture for receiving the support structures 310, 315. Such a configuration enables the support structures 310, 315 to move relative to the attachment pads 320, 325, 330, 335 to enable the apical distance L to be adjusted thereby controlling the position of a papillary muscle relative to an associated annuloplasty device or annulus.

Figure 4:
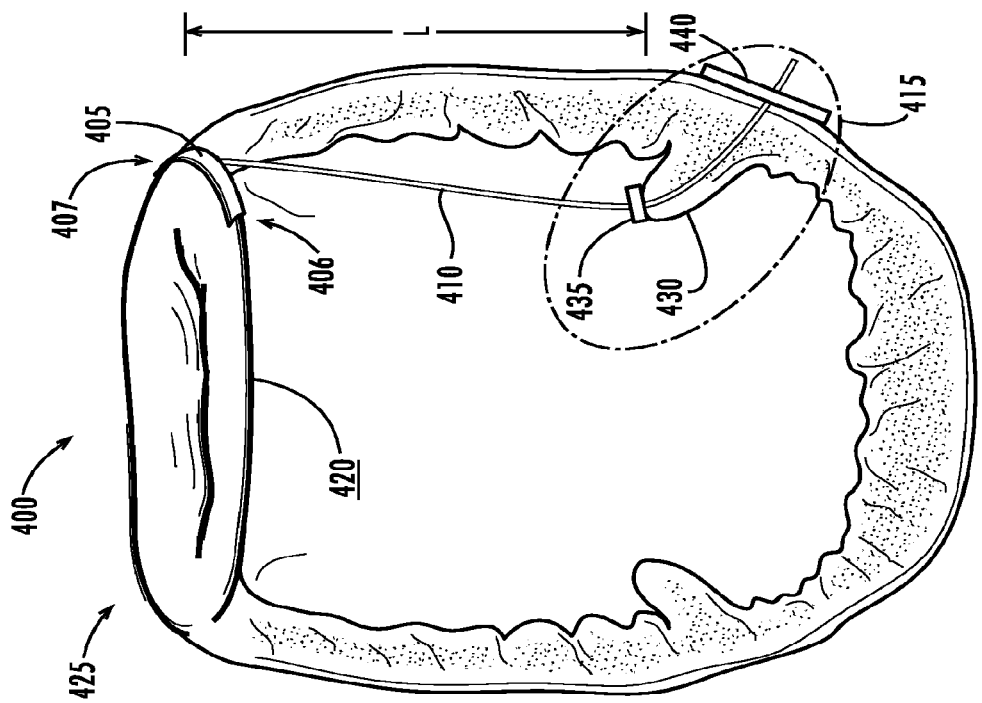
FIG. 4 illustrates a device to control the position of a papillary muscle including an annulus support anchor according to some embodiments of the present invention.

FIG. 4 illustrates a device 400 to control the position of a papillary muscle including an annulus support anchor according to some embodiments of the present invention. As shown, device 400 generally includes an annulus anchor 405, a support structure 410, and a papillary muscle attachment system 415. As shown, the annulus anchor 405 is coupled to an annulus 420 of an atrioventricular valve 425, and the papillary muscle attachment system 415 is coupled to a papillary muscle 430 of the atrioventricular valve 420. The device 400 can enable the apical distance L between the annulus 420 and the papillary muscle 430 to be adjusted thereby controlling the geometrical shape of the annulus 420 and its associated leaflets (not shown).

As shown, the support structure 410 is disposed between the annulus 420 and the papillary muscle 430. In some embodiments, the support structure 410 may directly anchor to the annulus 420 of the atrioventricular valve 420 (without the need for an annuloplasty ring) and in other embodiments, the support structure 410 can be coupled to an annuloplasty ring. The annulus anchor 405 can be many attachment mechanisms that enable the support structure 410 to be fixedly secured to the annulus 405. For example, such attachment mechanisms can include, but are not limited to, a single or a plurality of hooks, clamping surfaces, or an umbrella type device. Still yet, the annulus anchor 405 can have divergently extending arm members, such as arm members 406, 407, that can extend at least partially around the perimeter of the annulus 420. The arm members 406, 407 can have variable flexibilities to enable the support structure 410 to attach at various places along the annulus 405 or attach to various types of annuloplasty devices. The annulus anchor 405 may be permanently connected to the support structure 410 in some embodiments or may be detachably affixed such that the annulus anchor 405 and the support structure 410 can be detached and reattached numerous times.

As shown, the support structure 410 is also connected to the papillary muscle 430 via the papillary muscle attachment system 415. The papillary muscle attachment system 415 can comprise multiple pads, such as a first pad 435 and a second pad 440, enabling the papillary muscle attachment system 415 to be fixedly secured to or encompass the papillary muscle 430. For example, the first pad 435 and the second pad 440 can be sutured proximate the papillary muscle 430. Alternatively, the pads 435, 440 may not be secured directly to the papillary muscle 430 and may be slidably coupled to the support structure 410. Still yet, one or more of the pads can lockably engage the support structure 410 to a certain length to adjust the apical distance between the annulus 420 and the papillary muscle 430. This configuration can also enable the pads 435, 440 to be axially moved along the axis of support structure 410 to encompass the papillary muscle 430 to alter the shape of the papillary muscle 430.

The papillary muscle system 415 preferably enables movement of the papillary muscle 430 relative to the annulus 420. This movement can adjust the apical distance L and enables the geometry of the annulus to be altered in a manner to control, reduce, or eliminate regurgitation that may be associated with atrioventricular valve 425. The apical movement can occur in various manners according to the various embodiments of the present invention. For example, the section of the support structure 410 disposed between the annulus 420 and the papillary muscle 430 can be adjusted by moving the first pad 435 and the second pad 440 along the axis of the support structure. The first pad 435 and the second pad 440 can have interior apertures located within the first pad 435 and the second pad 440 that allow the support structure 410 to slidably pass through the first pad 435 and the second pad 440. Once the length of the support structure 410 has been adjusted to an appropriate amount that corresponds to an optimal apical distance modification, the pads 435, 440 can be used to fix the support structure the appropriate amount. Although the movement of the support structure 410 is discussed as movement based from the papillary muscle 430 other embodiments may utilize movement based from one or more of the annulus 420 and the annulus anchor 405.

One or both of the first pad 435 and the second pad 440 can also have locking mechanisms. A locking mechanism enable the pads 435, 440 to lock at a certain point along the axis of the support structure 410. Sample locking mechanisms can include, but are not limited to, threaded screw devices, pin locking devices, detent mechanisms, or many other mechanisms capable of applying pressure to the support structure 410. Advantageously, the locking feature enables the device 400 to be adjusted to fix the apical distance L to provide an optimal change to the morphology of the annulus 420 thereby enabling specific control and position of the papillary muscle 430 with respect to the annulus 420.

Figure 5:
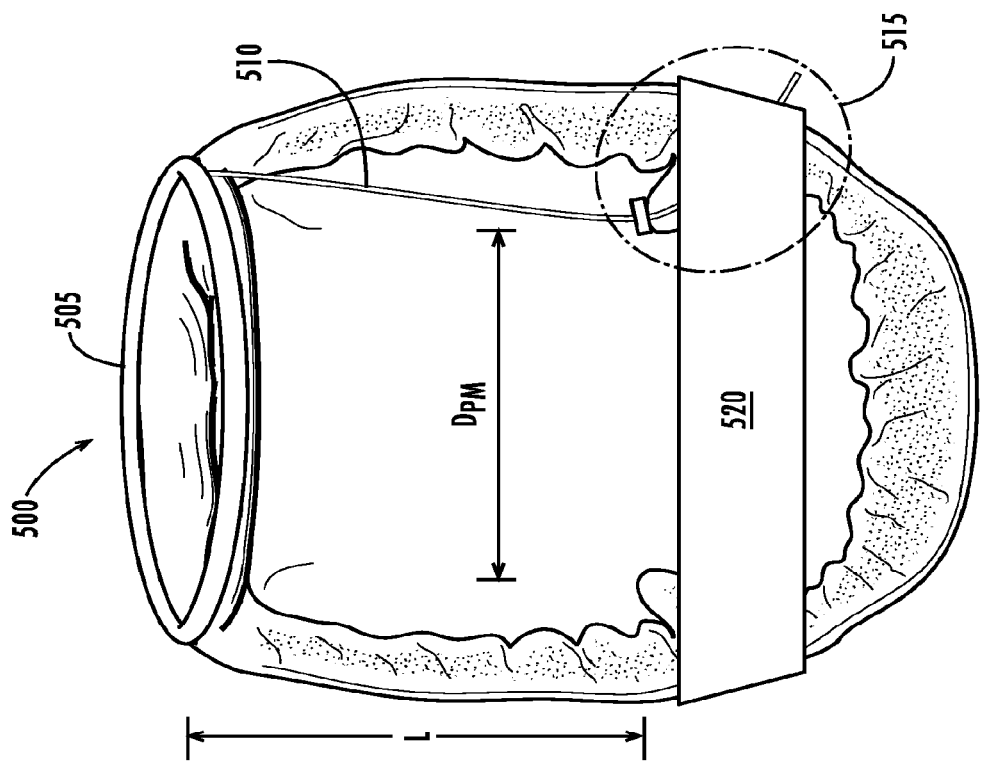
FIG. 5 illustrates a device to control the position of a papillary muscle including an annular ring and an external restraint according to some embodiments of the present invention.

FIG. 5 illustrates a device 500 to control the position of a papillary muscle according to some embodiments of the present invention. The device 500 generally includes an annular ring 505, a support structure 510, a papillary muscle attachment system 515, and a restraint 520. While the restraint 520 is illustrated as an external restraint (positioned outside a valve), the restraint 520 may also be an internal restraint positioned within a valve. For brevity, certain details of the annular ring 505, the support structure 510, and the papillary muscle attachment system 515 are not discussed in detail with device 500 as these items can have characteristics and details similar to the corresponding named components discussed herein. As shown in FIG. 5, the annular ring 505 is coupled to an annulus of a valve and the papillary muscle attachment system 515 enables a support structure 510 extending from the annular ring 505 to be fixedly attached to a papillary muscle. The restraint 520 partially blocks from view the papillary muscle attachment system 515 since the restraint 520 is an external restraint.

The annular ring 505 can have various characteristics. For example, the annular ring 505 may be a flexible ring, a rigid ring, or a multilink ring. The annular ring 505 may be complete or partial. Also, the ring 505 may have a saddle height to commissural ratio between approximately 0% and approximately 30%. In one preferred embodiment, the annular ring 505 can be composed of titanium wire, stainless steel, Nitnol, other biocompatible metals, or combinations thereof. In yet other embodiments, the annular ring 505 may be constructed of a biocompatible polymer. The annular ring 505 may be covered by a suturing cuff when coupled to an annulus of a valve. The cuff material may be Dacron or other biocompatible suture support polymers. The annular ring 505 may be attached to a valve annulus through suture, clamps, titanium clips, hooks, or many other anchoring mechanisms.

The annular ring 505, like rings of other embodiments, can be deployed using a variety of methods. For example, the annular ring 505 may be collapsed and delivered through a catheter endovascularly or through a long arm thorocoscopically. The annular ring 505, if partial, may be extended within a lumen of a catheter during delivery. If the annular ring 505 is composed of a series of links, it may be reversibly opened to deliver it using less invasive (or minimally invasive) methods according to some embodiments of the present invention.

The support structure 510 can also have a variety of characteristics. For example, the support structure 510 can be permanently attached to the annular ring 505. The support structure 510 can also be retractable, and anchored onto the annular ring 505 through a latching, locking, or screw mechanism. Other mechanisms to attach or couple the support structure 510 to the annular ring 505 include screws, clamping, knots, and clips. In one preferred embodiment, the support structure 510 can be a single or a plurality of elongated rods. The support structure 510 may be rigid, flexible, straight, or curved. Additionally the support structure 510 may be formed of a single or plurality of component materials. For example, the support structure 510 can be formed of a plurality of thin metal wires. The support structure 510 can be constructed using various materials, included but not limited to, titanium, stainless steel, biocompatible alloys, biocompatible polymers, gortex, silk, or other biocompatible materials.

As shown in FIG. 5, the device 500 includes a single support structure 510 and use of an annular ring 505. It should be understood, however, that other embodiments of the present invention encompass using multiple support structures 510 and not using an annular ring 505. For example, some embodiments comprise a single or a plurality of biocompatible support structures 510 which extend between a valve annulus and a papillary muscle or a ventricular wall. Thus, one end a support structure 510 can comprise an anchoring mechanism that can couple the support structure 510 to a valve annulus. The anchoring mechanism may consist of a series of hooks, clamps, expanding umbrella, or a memory alloy mesh.

FIG. 5 also illustrates how the restraint 520 can be provided around the exterior of an atrioventricular valve. The restraint 520 can be used to help control the lateral distance between papillary muscles (e.g., medial and lateral papillary muscles) and also in reshaping the exterior of a valve as it might grow or expand. This lateral distance is labeled as line $D_{PM}$ in FIG. 5. Controlling the lateral distance can assist in controlling the apical distance between papillary muscles and an associate valve annulus. It should be understood that a lateral distance control mechanism can also be used in accordance with other embodiments of the present invention. Other features of the restraint 520 can include restricting lateral growth of a valve wall by applying a radially inward force to the valve wall.

The restraint 520 can have additional characteristics. For example, the restraint 520 can be attached at multiple points along the exterior of a valve wall to control the distance between medial and lateral papillary muscles. As mentioned above, the restraint 520 can also be provided internally within a valve such that it can be disposed between medial and lateral papillary muscles. For example, in one configuration, an internal restraint can be a suture or other tension member that is coupled to the medial and lateral papillary muscles or at positions along the valve wall proximate the medial and lateral papillary muscles. The restraint 520 can be made from many materials, and can comprise one or more materials, including but not limited to, polymer materials, a metallic mesh, and cloth materials.

The restraint 520 can also have an adjustable length. For example, the ends of the restraint 520 may be fixedly secured to the papillary muscle attachment system 515. Adjustment of the length of the restraint 520 can occur when one or both ends of the restraint 520 are moved relative to the papillary muscle attachment system 515 thereby having a cinching effect to decrease the lateral distance $D_{PM}$. Also, in some embodiments, the papillary muscle attachment system 515 can comprise a locking or securing mechanism enabling the length of the restraint 520 to be fixed after an optimal length has been obtained. For example, a device can be at least partially located within a papillary muscle to enable the length of the restraint 520 to be adjusted and then clamped or pinned to have a certain length.

Figure 6:
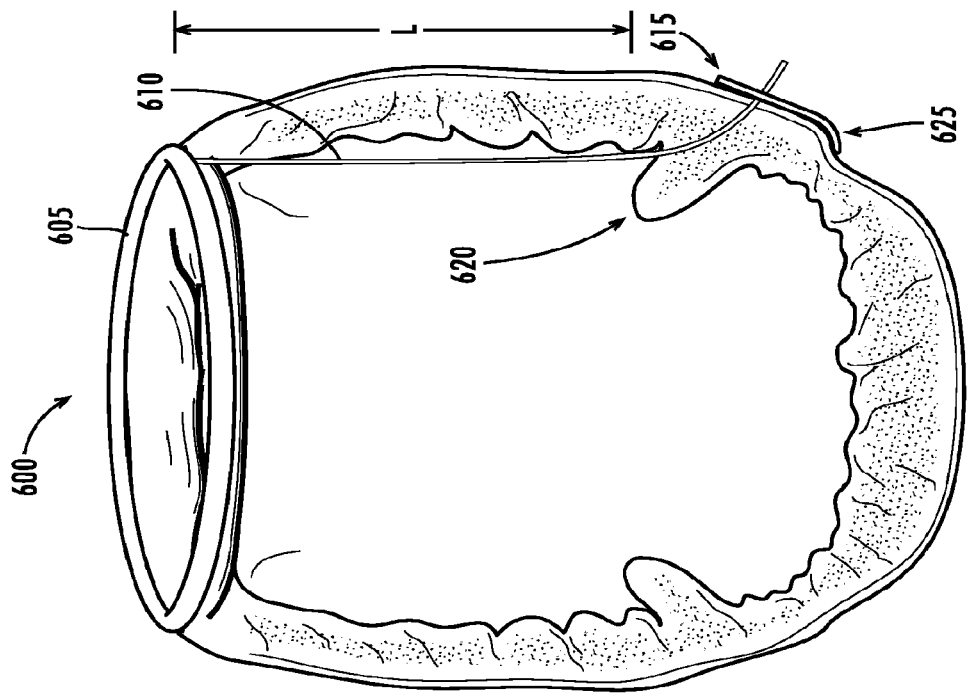
FIG. 6 illustrates a device to control a position of a papillary muscle including a support that does not penetrate a papillary muscle according to some embodiments of the present invention.

FIG. 6 illustrates a device 600 to control a position of a papillary muscle including a support structure that does not penetrate a papillary muscle according to some embodiments of the present invention. Generally, the device 600 comprises an annular ring 605, a support structure 610, and a ventrical wall pad 615. In this embodiment, the support structure 610 and the ventrical wall pad 615 are adapted so that the papillary muscle 620 is not penetrated by the support structure 610. Such a configuration may be advantageous when penetration of a papillary muscle may not be beneficial for a patient or when movement of a papillary muscle with respect to the support structure 610 may cause the device 600 to function improperly.

Because of the placement of the support structure 610 around the exterior of the papillary muscle 620, the shape of the ventrical wall pad 615 can be modified. As shown in FIG. 6, the ventrical wall pad 615 is shown to extend below the papillary muscle 620 such that it cups the exterior valve wall proximate the papillary muscle 620. Also, as shown, the ventrical wall pad 615 has a bottom end 625 that is curved to cup the exterior valve wall. Such configuration of the ventrical wall pad 615 ensures that pressure applied to the valve wall does not harm the valve wall or papillary muscle 620 and sufficiently controls the position of the papillary muscle 620.

As with other embodiments of the present invention, device 600 is preferably adapted so that the apical distance L between the annular ring 605 and the papillary muscle 620 can be adjusted. Adjusting this distance can occur by moving or sliding the ventrical wall pad 615 along the axis of the support structure 610. The ventrical wall pad 615, therefore, preferably includes a locking mechanism that enables the ventrical wall pad 615 to lock onto a certain point along the axis of the support structure 610. This advantageous features enables an optimal apical distance L to be obtained after deployment of device 600. For example, after device 600 is surgically deployed within a patient, the apical distance L can be modified such that regurgitation can be reduced or eliminated.

Figure 7:
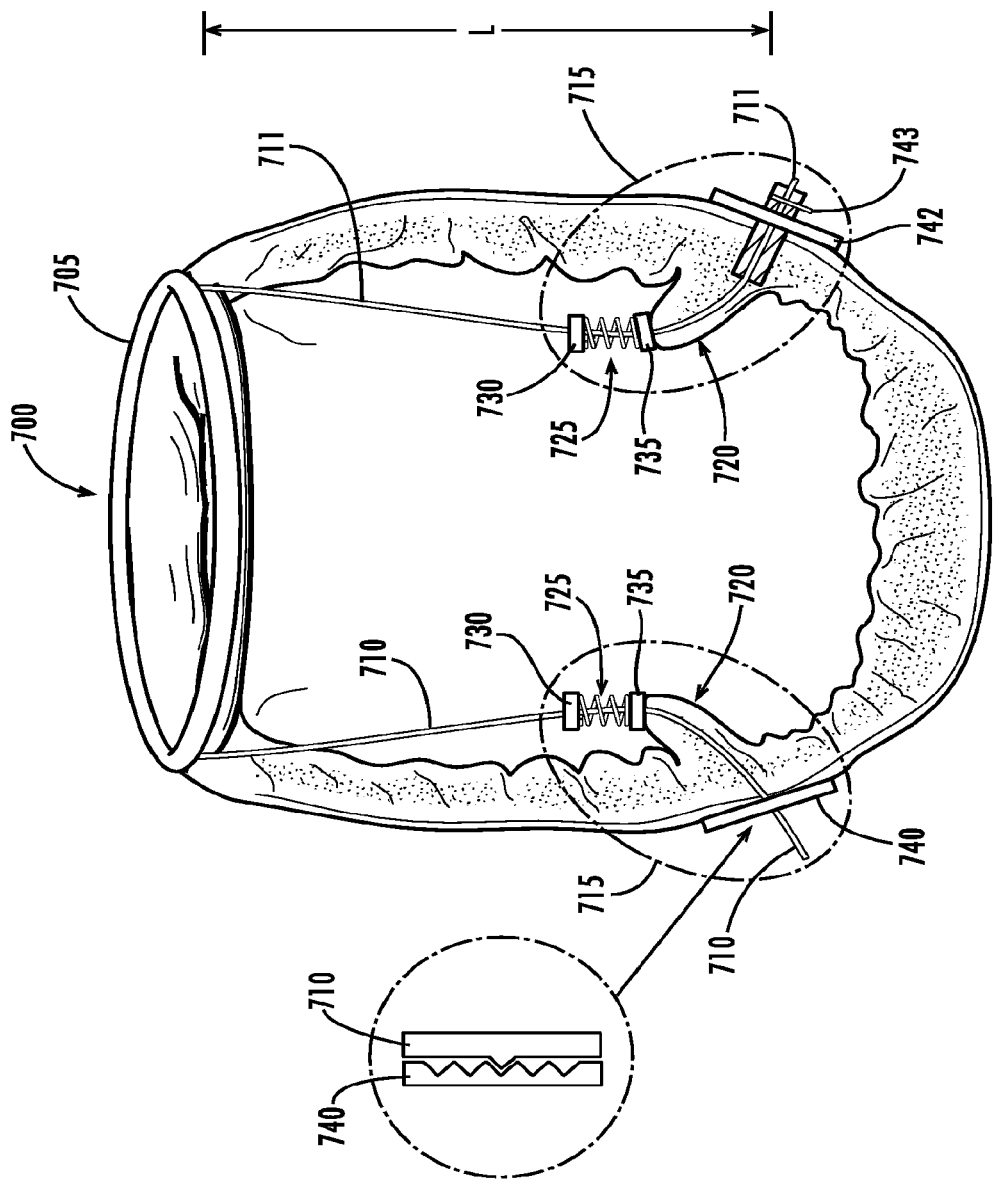
FIG. 7 illustrates a device to control a position of a papillary muscle including support structures having variable lengths according to some embodiments of the present invention.

FIG. 7 illustrates a device 700 to control a position of a papillary muscle using support structures having variable lengths according to some embodiments of the present invention. Generally, the device 700 comprises an annular ring 705, two support structures 710, 711 and an attachment system 715. The support structures 710, 711 are disposed between and coupled to the annular ring 705 and the attachment system 715. As shown, the attachment system is attached to papillary muscles 720. In other embodiments the attachment system 715 can be coupled to a ventricular wall. Also, the attachment system 715 may anchor to a ventricular wall by being coupled to inner or outer surfaces of a ventricular wall. The attachment system 715 may move axially along the length of the support structures 710, 711 to control the apical distance L between the papillary muscles 720 and the annulus ring 705.

The attachment system 715 can also comprise other components. These components can include a tension member 725 disposed between opposing end members 730, 735. The end members 730, 735 can each comprise apertures to receive the support structures 710, 711. This configuration enables the end members 730, 735 to compress the tension member 725 as the end members 730, 735 are moved along the axis of the support structures 710, 711. Advantageously, this configuration can also restrict axial movement of the papillary muscles 720 and/or can enable the length of the papillary muscles 720 to be controlled. Such a configuration may be desired if one of the papillary muscles 720 is damaged or does not properly function. According to some embodiments, the position of the attachment system 715 along the axis of the support structure may also be controlled externally, or outside of the heart. For example, a surgeon could insert an adjustment tool via minimally invasive process into a patient (with a beating heart) and use the tool to adjust, or fine tune, the length of the support structures 710, 711 to control and eliminate regurgitation.

In other embodiments, the attachment system 715 can be controlled remotely via a remote adjuster outside of a patient's body. Such a remote adjuster may transmit radio frequency signals, microwave signals, or other non-visible energy to activate or instruct the attachment system to adjust the length of on or more of the support structures 710. Thus, the attachment system 715 may comprise a signal receiver or transmitter to receive such instructions or transmit status information to a remote adjuster about the attachment system 715 or the patient. The attachment system 715 can also be used to decrease or increase via remotes means the length of the papillary muscles 720 by compressing the tissue between the tip of the papillary muscle 720 and a corresponding ventricular wall.

As mentioned above, the attachment system 715 may move axially along the length of the support structures 710, 711. To enable this advantageous feature, the attachment system 715 may comprise adjustable and lockable mechanisms, such as a first exterior pad 740 and a second exterior pad 742. As shown, the first exterior pad 740 is disposed on the exterior wall of the illustrated valve. The second exterior pad 742 has a first portion that is disposed on the exterior wall of the illustrated valve and a second portion that is partially disposed within the papillary muscle.

As shown in the close up illustrations of the pads 740, 742, they have features enabling the pads 740, 742 to lockably engage the support structures 710, 711. For example, the first pad 740 can have a notched interior aperture to receive a detent member formed on the support structure 710. An axial force applied to the support structure 710 can move detent member of the support structure 710 along the notched interior aperture. Also, the second pad 742 can have a pin clamp that lockably engages the support structure 711. The pin clamp can have a shaft to receive the support structure and a pin 743 that can be pushed toward and clamp the support structure. As the pads 740, 742 illustrate, some embodiments of the present invention can have support structure length adjustment mechanisms proximate papillary muscles.

Figure 8:
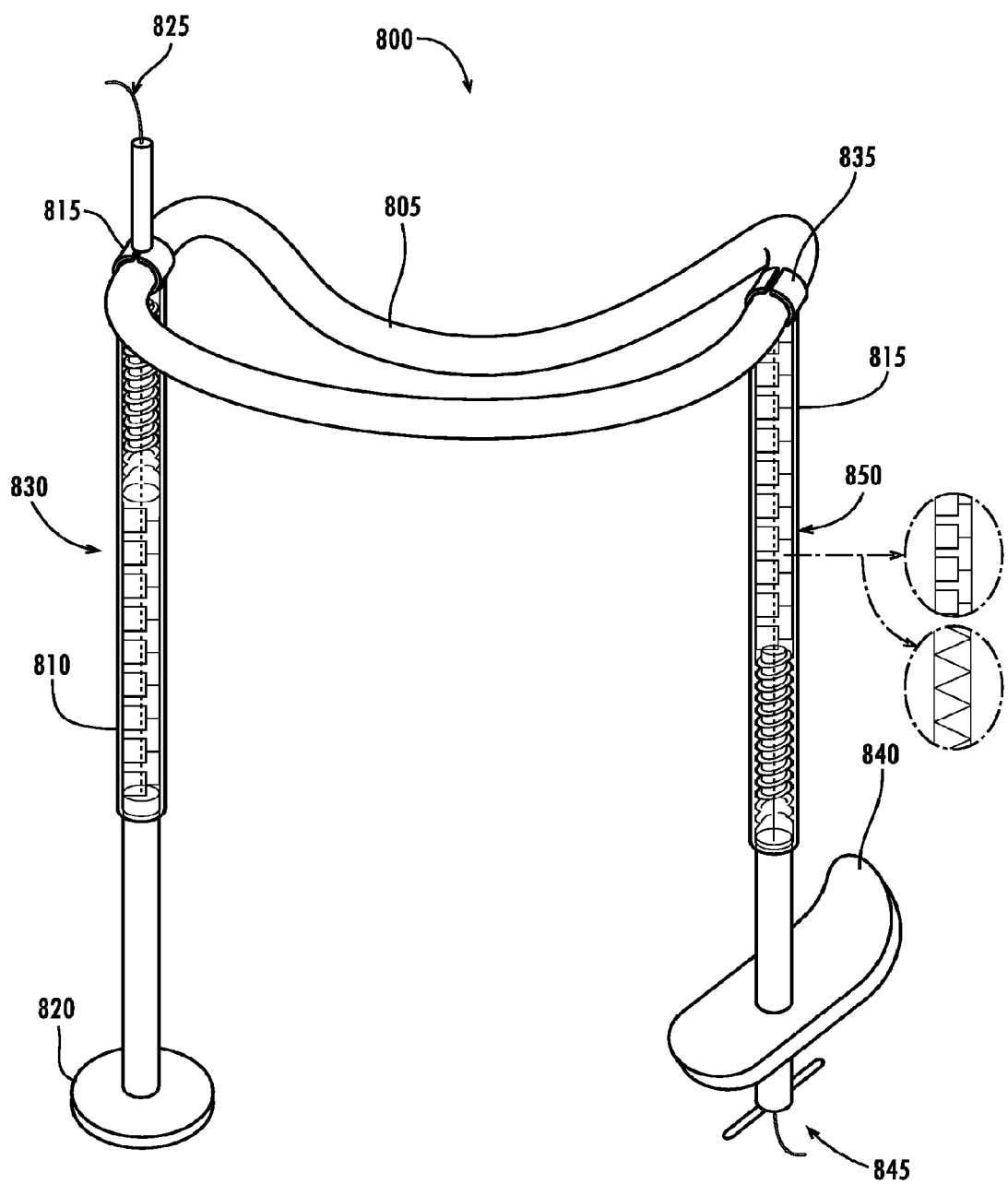
FIG. 8 illustrates a device to control a position of a papillary muscle including internally threaded support structures according to some embodiments of the present invention.

FIG. 8 illustrates a device 800 to control a position of a papillary muscle using internally threaded support structures according to some embodiments of the present invention. Device 800 generally comprises a first support structure 810, and a second support structure 815. The device 800 may also comprise annular saddle ring 805 in accordance with some embodiments of the invention. The device 800 can be deployed in an atrioventricular valve to control, reduce, and eliminate mitral regurgitation associated with the atrioventricular valve by reducing the apical distance between the atrioventricular valve's annulus and papillary muscles. The annular saddle ring 805 can be sutured or otherwise attached to the annulus, and the support structures 810, 815 can be extended in a valve to the valve's papillary muscles. The support structures 810, 815 can be coupled to the annular saddle ring 805 via clamps 815, 835 or many other anchoring or coupling mechanisms. The support structures 810, 815 may be covered with a biocompatible material (such as Goretex) and pierce or penetrate through the valve's papillary muscles and connect to exterior pads 820, 840 located outside of the valve's muscle wall.

The support structures 810, 815 can be adapted such their lengths can be adjusted. Adjustment of the lengths of the support structures 810, 815 can be utilized to vary the distance between the annular saddle ring 805 and the exterior pads 820, 840. Variation of this distance between the annular saddle ring 805 and the exterior pads 820, 840 in turn modifies the apical distance between the valve's annulus and papillary muscles. Apical distance modification can result in reshaping the morphology and geometry of the valve's annulus thereby enabling the leaflets of the annulus to move closer together.

The support structures 810, 815 can have interiors that enable the length of the support structures to be modified. For example, support structure 810 can have an interior 830 with detent members that enable movement and locking of the interior with corresponding apertures when a force is applied to an axial force interface member 825. For example, the axial force interface member can be a suture or a wire and when subjected to an axial force, the length of the support structure 810 can be reduced so that the annulus saddle ring 805 and the exterior pad 820 are moved closer together.

Similarly, support structure 815 can have a threaded interior that enables rotation of one end of the support structure 815 to be rotated to adjust the length of the support structure 815. This threaded interior configuration 830 can enable the length of the support structure 815 to be increased and decreased. According to some embodiments, support structure 830 may have a lever 845 at one end corresponding to pad 840 and rotation of the lever 845 may cause the length of the support structure 815 to change. In other embodiments, a screw can be used in the place of the lever 845 and rotation of the screw can cause the length of support structure 815 to be modified.

The support structures 810, 815 can also have certain internal flexibility characteristics. For example, the support structures 810, 815, as illustrated, can have internal spinal structures that enable the support structures to flex inward toward each other. Also, the support structures 810, 815 can have internal spinal structures that do not permit the support structures to flex away from each other. In other embodiments, the support structures 810, 815 can restrict lateral motion from one or more of the atrial or ventricular sides within a heart's mitral valve. Such an advantageous feature can, for example, aid in preventing growth of a heart's ventricle valve wall thus enabling the support structures 810, 815 to assist in controlling the position of one or more papillary muscles.

Exemplary internal spinal structures can comprise a unidirectional bending structure. This type of bending structure can comprise a plurality of internal components that taper away from the non-flexing direction. By tapering in the direction of the flexing direction, the internal spinal structures enable the support structure 810, 815 to compress. In one configuration, the plurality of internal components can generally have a triangular shape. In another configuration, the internal components can have a cross-section shaped as a "T". Advantageously, restricting the support structure from flexing can aid in shaping a valve wall and also implanting the device 800 within a patient.

The support structures 810, 815 may also comprise internal security characteristics. As the support structures 810, 815 may fracture or break, a security wire may be disposed within the support structures 810, 815. The security wire may transverse the entire interior length of the support structures 810, 815. Advantageously, a security wire can hold together or collocate any fracture support structure 810, 815 pieces because they will be disposed generally around the security wire.

Figure 9:
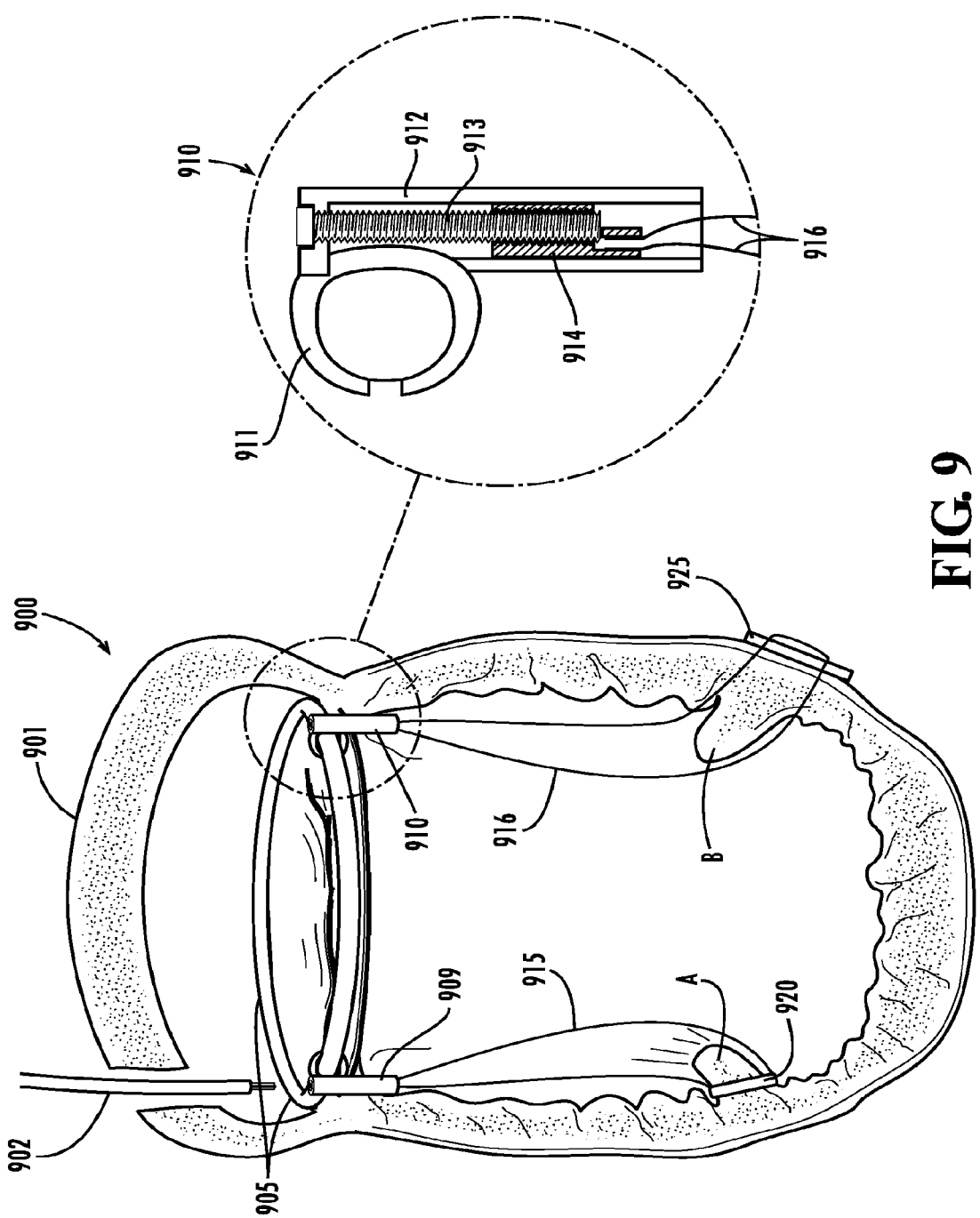
FIG. 9 illustrates yet another device to control a position of a papillary muscle according to some embodiments of the present invention.

FIG. 9 illustrates yet another device 900 to control a position of a papillary muscle according to some embodiments of the present invention. The device 900 enables adjustment of the position of two papillary muscles of the mitral valve through the atrium 901 with an adjustment tool 902. Generally, the device 900 comprises an annular ring 905 coupled to papillary muscles A, B via sutures 915, 916 as shown in FIG. 9. The device 900 also comprises adjustment mechanisms 909, 910, papillary muscle pad 920, and ventricle wall pad 925. The adjustment mechanisms 909, 910 can be used to adjust the length of the sutures 915, 916. Adjusting the length of the sutures 915, 916 can change the position of the papillary muscles A, B such that they are closer to the annular ring 905 and the annulus of the mitral valve. The adjustment mechanisms 909, 910 may be situated proximate the annulus, the papillary muscles A, B, or both such that adjustment to the length of the sutures 915, 916 can be performed in multiple locations.

In some embodiments, adjustment mechanisms 909, 910 may be remotely adjusted from outside of the body. For example, a remote adjuster (not shown) can be used to activate the adjustment mechanisms 909, 910. The remote adjuster may transmit radio frequency signals, microwave signals, heat energy, or other invisible energy to the adjustment mechanisms 909, 910. The adjustment mechanisms 909, 910 can receive such items and, in response, automatically activate the adjustment mechanisms 909, 910 to adjust the length of the sutures 915, 916. Also, the adjustment mechanisms 909, 910 may transmit status information outside of the body to inform about the status of the patient, device 900, adjustment mechanisms 909, 910, and/or the sutures 915, 916.

The components of device 900 can be implanted within a mitral valve to reduce, control, and eliminate mitral valve regurgitation. The annular ring 905 can be sutured to the annulus of the mitral valve. The annular ring 905 can be used to change the shape of the annulus and may not be used in all embodiments. The adjustment mechanisms 909, 910 can be securely coupled to the annular ring 905. In this embodiment, the adjustment mechanisms are clamped to the annular ring 905. The adjustment mechanism 909, 910 preferably include internal devices that enable the length of the sutures 915, 916 to be altered. Also, as shown, both of the adjustment mechanisms are located proximate the atrium of the illustrated mitral valve so that they can be adjusted through the atrium. For example, an adjustment tool 902 can be inserted through the atrium 901, as shown, to adjust the length of sutures 915, 916. Having the adjustment mechanisms 909, 910 located proximate the atrium 901 advantageously enables access to the adjustment mechanisms 909, 910 during surgery or post-operative procedures. In other embodiments, the adjustment mechanisms can be located proximate to one or both of the papillary muscles A, B.

As shown in the close up view of adjustment mechanism 910, an adjustment mechanism according to certain embodiments of the present can comprise various components. As shown, the adjustment mechanism 910 can generally include a clamp 911, a housing 912, an internal threaded bolt 913, and an internal thread nut 914. The internal thread nut 914 can include attachment points so that the suture 916 can be securely attached to the adjustment mechanism 910. The clamp 911 enables the adjustment mechanism 910 to be securely attached to an annulus or annuloplasty device.

As shown, the housing 912 houses the internal threaded bolt 913 and the internal thread nut 914. The internal thread bolt 913 can be countersunk into the housing 912. The internal thread bolt 912 can also be rotatably affixed to the housing 912 so that the internal thread bolt 919 can rotate within the housing 912. In this exemplary embodiment, the internal threaded bolt 913 can have a head to communicate with or that corresponds to adjustment tool 902. This enables the adjustment tool 902 to transfer a mechanical torque force to the threaded bolt 913 for rotation of the threaded bolt 913. The internal thread nut 914 can be disposed within the housing. The internal thread nut 914 can be interlocked or in communication with the internal thread bolt 913. As shown, the internal thread nut can be situated proximate and between opposing inner walls of the housing 912. Rotation of the internal thread bolt 913 causes the internal thread nut 914 to move along the length of the internal thread bolt 913. In some embodiments, the internal thread nut 914 may be adapted to between approximately 0.1 centimeters to approximately 5 centimeters. Also, the internal the internal thread bolt 913 and the internal thread nut 914 may have very fine thread pitch counts to enable precise specific movements thereby translating into very precise changes in the length of the suture 916.

FIG. 9 also illustrates a specific placement of the papillary muscle pad 920 which can be utilized in accordance with some embodiments of the present invention. The papillary muscle pad 920 can be used to attach the suture 915 to papillary muscle A. The papillary muscle pad 920, as shown, can be a collar-type device situated proximately around the exterior of the base of papillary muscle A. Alternatively, the papillary muscle pad 920 may be located at other positions along the exterior of or at the tip of papillary muscle A. In this embodiment, the papillary muscle pad 920 is located in the interior of the mitral valve so that surrounding areas of the heart are not affected, but in other embodiments, the papillary muscle pad 920 may be located outside of the mitral valve proximate papillary muscle A.

Device 900 also illustrates how a ventrical pad (ventrical wall pad 925) may be disposed or positioned on the exterior of the mitral valve according to some embodiments of the present invention. Indeed, as shown, the ventrical wall pad 925 is along the exterior of the mitral valve proximate papillary muscle B. The ventrical wall pad 925 can be sutured or otherwise attached to the exterior wall of the mitral valve at this position. Alternatively, the ventricle wall pad 925 may be affixed in place via the suture 916. The ventricle wall pad 925 can have multiple apertures to receive suture 916. Adjustment of the length of the suture 916 by reduction can result in cinching effect on papillary muscle B by a force applied to the ventrical wall pad 925. This cinching effect along with a reduction in the length of the suture 916 can control the apical position of the papillary muscle B, and move the papillary muscle B closer to the annulus of the mitral valve.

As shown in FIG. 9, the sutures 915, 916 generally couple the annulus of the mitral valve to the papillary muscles A, B. More specifically, the sutures 915, 916 connect the adjustment mechanisms 909, 910 (which are coupled to the annulus) to the pads 920, 925 (which are coupled to the papillary muscles A, B). The sutures 915, 916 are shown in a looped configuration, wherein the sutures 915, 916 are looped around or through the pads 920, 925 and the ends of the sutures 915, 916 are connected to the adjustment mechanisms 909, 910. In other embodiments, the sutures 915, 916 may not be looped. Alternatively, other support members can be used in the place of or in concert with the sutures 915, 916, including, but not limited, to wires, elongated rods, biocompatible metal, biocompatible polymer, biocompatible silk, other biocompatible materials, collagen, bio-engineered chords, or other bio-engineered materials.

Figure 10:
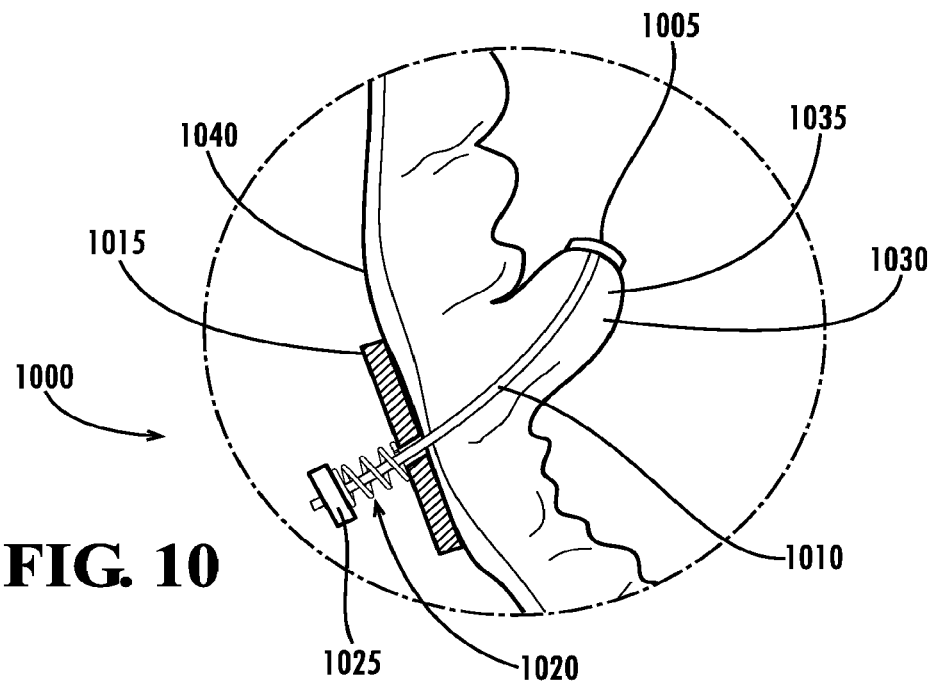
FIG. 10 illustrates a device to control a position of a papillary muscle including a compression force system according to some embodiments of the present invention.

FIG. 10 illustrates a device 1000 to control a position of a papillary muscle using a compression force according to some embodiments of the present invention. The device 1000 generally comprises an interior pad 1005, a support structure 1010, an exterior pad 1015, a tension member 1020, and a tension control member 1025. As shown, the interior pad 1005 can be proximate a tip 1030 of the papillary muscle 1035. The support structure 1010 can extend from the interior pad 1005 through the papillary muscle 1035 to the exterior of a valve wall 1040. The exterior pad 1015 can be positioned proximate the exterior of the valve wall 1040 and the tension member 1025 can be disposed between the exterior pad 1015 and the tension control member 1025. The support structure 1010 can be coupled to one surface of the interior pad 1005, and be placed within apertures located within the exterior pad 1015 and the tension control member 1025.

The length of papillary muscle 1035 can be controlled using the device 1000. For example, tension control member 1025 can be adjusted to move closer to the interior pad 1005 and such movement can decrease the length of the support structure 1010 between interior and exterior pads 1005, 1015. This decreased length in turn can compress the papillary muscle 1035 in a manner that can control the tip 1030 of the papillary muscle 1035 relative to an associated annulus.

The device 1000 can have various applications according to embodiments of the present invention. The device 1000 can be used as a stand alone device or in conjunction with a device such as that illustrated in FIG. 4 with a single support structure. In such a configuration, the devices 400, 1000 can form a system which can compress a first papillary muscle to control the position of a valve annulus in addition to apically adjusting a second papillary muscle. The device 1000 can also be used to control the length or shape of a papillary muscle in some embodiments.

Figure 11:
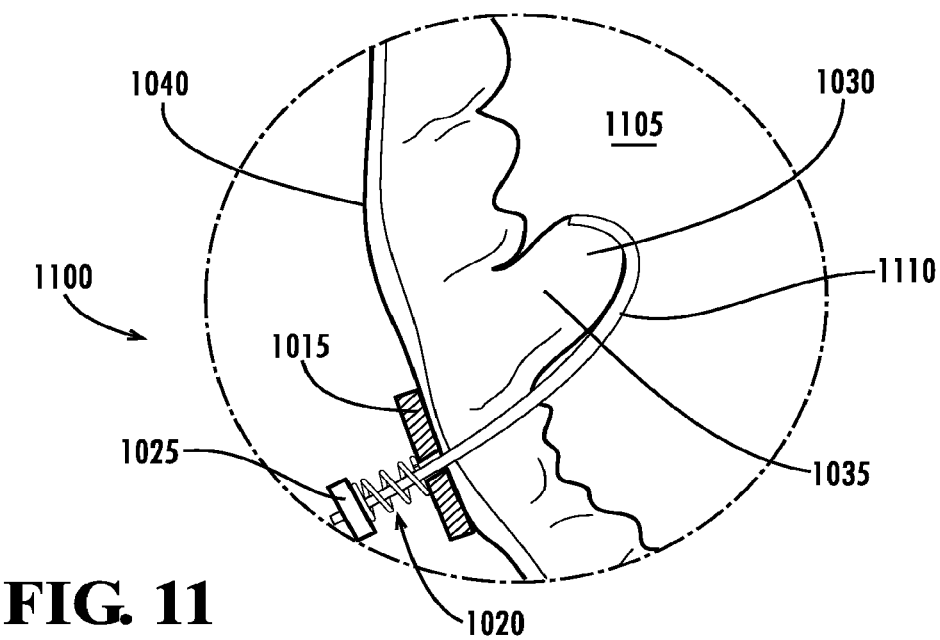
FIG. 11 illustrates a device to control a position of a papillary muscle including another compression force system according to some embodiments of the present invention.

FIG. 11 illustrates a device 1100 to control a position of a papillary muscle using a compression force according to some embodiments of the present invention. The device 1100 is similar in operation to the device 1000 illustrated in FIG. 10, so for brevity the same reference numerals are used in FIG. 11 for corresponding features shown and described above with reference to FIG. 10. One difference between FIG. 10 and FIG. 11 is that the support structure 1010 in FIG. 10 penetrates the papillary muscle 1035 and the support structure 1010 in FIG. 9 does not penetrate the papillary muscle 1035. Rather, the support structure 1110 of device 1100 illustrated in FIG. 11 is positioned along the exterior of the papillary muscle 1035. This configuration is beneficial and advantageous because it may be desired when penetrating a papillary muscle is not required. Also, this configuration may be desired to assist in controlling a papillary muscle having reduced functionality. The support structure 1110 of device 1100 can also be different in that it can have an interior pad 1105 that curves around the tip 1030 of the papillary muscle 1035 as shown in FIG. 11.

Figure 12:
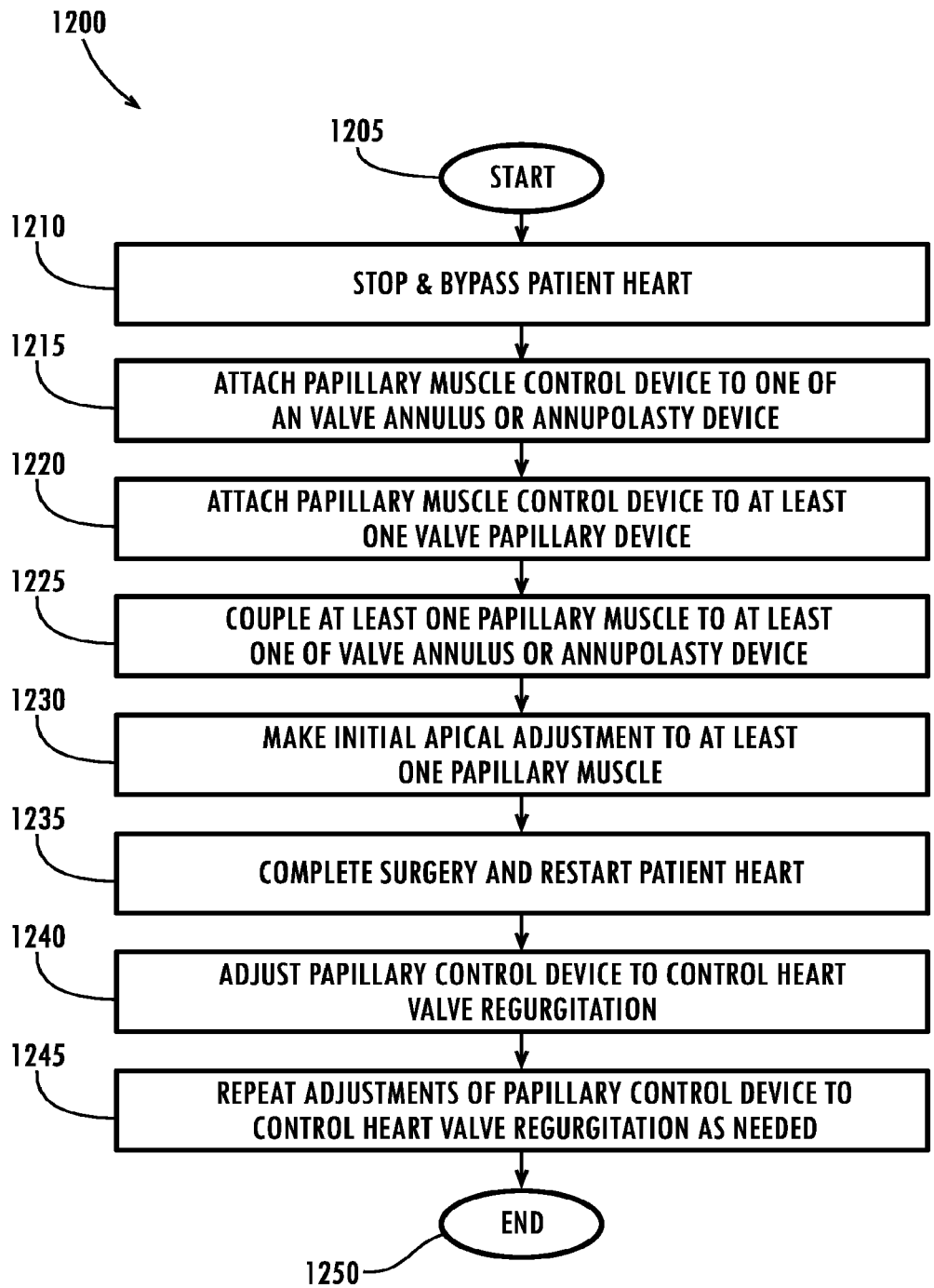
FIG. 12 illustrates a logical flow diagram depicting a method embodiment of the present invention capable of reforming an atrioventricular valve by controlling position of an associated papillary muscle.

FIG. 12 illustrates a logical flow diagram depicting a method 1200 embodiment of the present invention capable of reforming a mitral valve by controlling position of an associated papillary muscle. According to some method embodiments the complete implant or partial sections may be delivered percutaneously, and in other embodiments, the complete implant or partial sections may be delivered thoroscopically in a beating heart. Those skilled in the art will understand that the method 1200 is only one method embodiment of the present invention and that the method 1200 can have various steps or be performed in various orders.

The method 1200 can initiate at 1205 during a surgical operation being performed on a patient. The surgical operation may be an open heart surgery to fix or repair a patient's heart or to correct regurgitation associated with an atrioventricular valve, such as a mitral valve. In other embodiments, the surgical operation may be performed utilizing minimally invasive techniques in which surgical implants are inserted into a patient using lumens. The method 1200 can continue at 1210 where a patient's heart may be stopped and bypassed by a surgeon so that a papillary muscle control device can be deployed or implanted within the patient's heart. The method 1200 may also be performed on a beating heart and in such an instance and bypass of the heart may not occur.

Next, the papillary muscle control device can be deployed within a patient's heart in an effort to control, reduce, and eliminate regurgitation. The papillary muscle control device can be one of the exemplary embodiments discussed above, such as those illustrated in FIGS. 2-11. The papillary muscle control device may be implanted in a variety of manners and the implantation may depend on the utilized surgical procedure, health of the patient, or other factors. For example, and according to the method 1200, that papillary muscle control device may be attached (or anchored) to at least one of a valve annulus or an annuloplasty device at 1215.

That is, in some embodiments, the papillary muscle control device may be directly attached to a valve annulus, attached directly to an annuloplasty device, or both. The papillary muscle control device can be anchored using clamps, sutures, hooks, crimps, or other coupling mechanisms. If attached to an annuloplasty device, the papillary muscle control device may be permanently coupled to the annuloplasty device or capable of being attached and reattached to the annuloplasty device. Also, the annuloplasty device may be pre-implanted within a patient or implanted during the method 1200.

After the papillary muscle control device is connected to at least one of a valve annulus or an annuloplasty device, the papillary muscle control device can then be connected to at least one papillary muscle at 1220. Connecting the papillary muscle control device in this manner in turn couples at least one papillary muscle to at least one of a valve annulus or annuloplasty device at 1225. Advantageously, connecting the papillary muscle control device in this manner can adjust or move a papillary muscle to rectify abnormal movement of the papillary muscle. Indeed, connecting the papillary muscle control device to a papillary muscle enables the position of the papillary muscle to be controlled and moved apically toward a valve annulus so that an initial apical adjustment occurs at 1230. The inventors have discovered that controlling the movement of a papillary muscle in an apical direction can alter leaflet geometry.

The papillary muscle control device can have various connection and functional characteristics. For example, the papillary muscle control device can have multiple connection structures. These multiple connection structures can enable connection or coupling between a valve annulus and to two papillary muscles. Also, the papillary muscle control device preferably comprises connection structures capable of having adjustable lengths. For example, the connection structures themselves can incorporate multiple parts that interact to alter the length of the connections structures (e.g., an interior threaded configuration). Alternatively, the papillary muscle control device can have length adjustment mechanism that adjust the apical distance between a papillary muscle and valve annulus by movement along the length of a support structure.

The length adjustment mechanism can interact with (e.g., slidably engage) a support structure so that the apical distance can be varied to an optimal length. The optimal length may be the length that eliminates regurgitation or controls regurgitation to a sufficient amount. The length adjustment mechanism can also have a locking mechanism (e.g., pin lock, detent member, or clamp) that can fix the length of the support structure at the optimal length. The length adjustment mechanism can be located proximate a valve annulus, proximate a papillary muscle, or both according to the various embodiments of the present invention. Thus, the length adjustment mechanism can be utilized to adjust the length of a support structure so that the apical distance between a papillary muscle and valve annulus is modified to reduce regurgitation.

After implantation of the papillary muscle control device, the surgical operation can be completed at 1235. If the surgical operation required stopping of a patient's heart, then the patient's heart can be restarted at this time. Preferably, the patient's heart will then be allowed to operate for approximately five minutes so that the function of the heart at this time can be close to normal operation. After waiting, further adjustments can be made to the papillary muscle control device at 1240. These adjustments, for example, can be made as a surgeon analyzes Doppler regurgitation results. Advantageously, this feature enables fine tuning of the papillary muscle control device on a beating heart. Also this feature enables apical adjustment of a papillary muscle in real time while monitoring regurgitation data to control, reduce, or eliminate regurgitation.

It should be understood that these further adjustments can be made at any time post-operation. For example, after waiting several minutes, a surgeon can perform the adjustments. Alternatively, the adjustments to the papillary muscle control device may occur days, months, or years after successful conclusion of a surgery and after a patient has healed. This would enable a surgeon to use minimally invasive procedures to access the papillary muscle control device to alter the length of a support structure thereby altering the apical distance of a papillary muscle relative to a valve annulus. Thus, adjustments to the papillary muscle control device can be repeated at 1245 as needed to control heart valve regurgitation at 1245 to complete method 1200 at 1250.

The embodiments of the present invention are not limited to the particular exemplary embodiments, process steps, and materials disclosed herein as such embodiments, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Thus, while the various embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

We claim:

1. A method for treating mitral valve disease in a heart, the method comprising:
   accessing a heart by minimally invasive surgery;
   fixing a first anchor at a mitral valve in a heart, the first anchor including a cover comprising a suturable layer;
   extending a suture of at least one support structure through a left ventricular wall, a first end of the at least one support structure secured to the first anchor;
   positioning a second anchor against an exterior of the left ventricular wall, the second anchor including an aperture through which the suture slidably extends;
   adjusting a length of the at least one support structure between the first anchor and the second anchor while monitoring an effect of the adjusting on the beating heart, wherein the adjusting includes sliding the suture relative to the second anchor; and
   locking the suture at the second anchor, thereby fixing the length of the at least one support structure between the first anchor and the second anchor, wherein locking the suture includes engaging the suture with a locking mechanism of the second anchor.

2. The method of claim 1, wherein fixing the first anchor includes attaching the first anchor to an annulus of the mitral valve.

3. The method of claim 1, wherein extending the suture of the at least one support structure includes extending a suture of a first support structure and a suture of a second support structure.

4. The method of claim 1, wherein positioning the second anchor includes positioning a second anchor including a portion curved to cup the exterior ventricular wall.

5. A method for treating a diseased atrioventricular valve in a heart comprising:
fixing a first anchor at an atrioventricular valve in a heart;
extending a support structure through a ventricular wall, a first end of the support structure secured to the first anchor;
positioning a second anchor against an exterior of the ventricular wall, the second anchor including an aperture through which the support structure slidably extends;
adjusting a length of the support structure between the first anchor and the second anchor while the heart is beating; and
locking the support structure at the second anchor, thereby fixing the length of the support structure between the first anchor and the second anchor.

6. The method of claim 5 further comprising accessing the heart by minimally invasive surgery.

7. The method of claim 5, wherein fixing the first anchor at the atrioventricular valve includes fixing the first anchor at a mitral valve.

8. The method of claim 5, wherein fixing the first anchor includes attaching the first anchor to an annulus of the atrioventricular valve.

9. The method of claim 8, wherein attaching the first anchor includes attaching an annuloplasty ring.

10. The method of claim 5, wherein fixing the first anchor includes fixing a first anchor including a cover comprising a suturable layer.

11. The method of claim 5, wherein extending the support structure through a ventricular wall includes extending a suture of the support structure through the ventricular wall.

12. The method of claim 5, wherein extending the support structure includes extending the support structure through or proximate to a papillary muscle.

13. The method of claim 12, wherein extending the support structure through or proximate to the papillary muscle includes extending the support structure through a pad contacting the papillary muscle or inner ventricular wall.

14. The method of claim 5, wherein extending the support structure includes extending a first support structure and a second support structure.

15. The method of claim 5, wherein positioning the second anchor includes positioning a second anchor including a portion curved to cup the exterior ventricular wall.

16. The method of claim 5, wherein adjusting the length of the support structure further comprises monitoring an effect of the adjusting on the beating heart.

17. The method of claim 16, wherein monitoring the beating heart includes monitoring the beating heart by Doppler.

18. The method of claim 5, wherein locking the support structure includes engaging the support structure with a locking mechanism of the second anchor.

* * * * *